US011327004B2

(12) United States Patent
Meldrum et al.

(10) Patent No.: US 11,327,004 B2
(45) Date of Patent: May 10, 2022

(54) LIVE-CELL COMPUTED TOMOGRAPHY

(71) Applicant: ARIZONA BOARD OF REGENTS ON BEHALF OF ARIZONA STATE UNIVERSITY, Scottsdale, AZ (US)

(72) Inventors: Deirdre Meldrum, Phoenix, AZ (US); Roger Johnson, Phoenix, AZ (US); Laimonas Kelbauskas, Gilbert, AZ (US); Jeff Houkal, Los Angeles, CA (US); Brian Ashcroft, Mesa, AZ (US); Dean Smith, Phoenix, AZ (US); Hong Wang, Tempe, AZ (US); Shih-Hui Joseph Chao, Phoenix, AZ (US); Rishabh Shetty, Tempe, AZ (US); Jakrey Myers, Scottsdale, AZ (US); Iniyan Soundappa Elango, Hillsboro, OR (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 242 days.

(21) Appl. No.: 16/082,170

(22) PCT Filed: Mar. 2, 2017

(86) PCT No.: PCT/US2017/020528
§ 371 (c)(1),
(2) Date: Sep. 4, 2018

(87) PCT Pub. No.: WO2017/151978
PCT Pub. Date: Sep. 8, 2017

(65) Prior Publication Data
US 2019/0346361 A1 Nov. 14, 2019

Related U.S. Application Data

(60) Provisional application No. 62/302,649, filed on Mar. 2, 2016.

(51) Int. Cl.
*G01N 15/14* (2006.01)
*G01N 21/47* (2006.01)
*G01N 21/17* (2006.01)

(52) U.S. Cl.
CPC ..... *G01N 15/1436* (2013.01); *G01N 15/1468* (2013.01); *G01N 21/4795* (2013.01); *G01N 2021/1787* (2013.01)

(58) Field of Classification Search
None
See application file for complete search history.

(56) References Cited

U.S. PATENT DOCUMENTS 5,170,890 A * 12/1992 Wilson ................. B01D 59/34
209/11
5,402,460 A 3/1995 Johnson
(Continued)

FOREIGN PATENT DOCUMENTS

WO 2010022391 A9 2/2010
WO 2010042478 A2 4/2010
(Continued)

OTHER PUBLICATIONS

Wang et al "Rotation of Cells and Cell Clusters in Culture Media for Optical Computed Tomography", Center for Biosignatures Discovery Automation, Biodesign Institute, Arizona State University, 17th International Conference on Miniaturized Systems for Chemistry and Life Sciences, Oct. 27-31, 2013.*
(Continued)

*Primary Examiner* — Shawn Decenzo
*Assistant Examiner* — Jarreas C Underwood
(74) *Attorney, Agent, or Firm* — Quarles & Brady LLP

(57) ABSTRACT

Systems and methods of using the same for functional fluorescence imaging of live cells in suspension with isotropic three dimensional (3D) diffraction-limited spatial
(Continued)

resolution are disclosed. The method-live cell computed tomography (LCCT)-involves the acquisition of a series of two dimensional (2D) pseudo-projection images from different perspectives of the cell that rotates around an axis that is perpendicular to the optical axis of the imaging system. The volumetric image of the cell is then tomographically reconstructed.

13 Claims, 17 Drawing Sheets

(56) References Cited

U.S. PATENT DOCUMENTS

| | | | |
|---|---|---|---|
| 5,530,551 A * | 6/1996 | Cantrall | G01N 33/362 356/394 |
| 5,999,836 A * | 12/1999 | Nelson | A61B 5/0091 250/339.02 |
| 6,056,861 A | 5/2000 | Fuhr | |
| 6,781,688 B2 * | 8/2004 | Kren | G01N 21/9501 356/237.1 |
| 6,944,322 B2 | 9/2005 | Johnson | |
| 7,738,695 B2 | 6/2010 | Shorte | |
| 8,748,192 B2 | 6/2014 | Tian | |
| 8,811,691 B2 * | 8/2014 | Freifeid | G01N 21/952 382/128 |
| 9,181,375 B2 | 11/2015 | Tian | |
| 9,410,970 B2 | 8/2016 | Tian | |
| 9,597,026 B2 | 3/2017 | Meldrum | |
| 10,022,718 B2 | 7/2018 | Martineau | |
| 10,042,369 B2 * | 8/2018 | Blackley | G05D 7/0688 |
| 10,156,573 B2 | 12/2018 | Tian | |
| 10,162,162 B2 | 12/2018 | Wang | |
| 10,221,443 B2 | 3/2019 | Meldrum | |
| 10,229,338 B2 * | 3/2019 | Nonaka | G06K 9/4638 |
| 2001/0023324 A1 | 9/2001 | Pronovost | |
| 2003/0199758 A1 | 10/2003 | Nelson | |
| 2004/0076319 A1 | 4/2004 | Fauver et al. | |
| 2005/0049486 A1 * | 3/2005 | Urquhart | A61B 34/20 600/429 |
| 2006/0150968 A1 * | 7/2006 | Rabinowitz | F24S 23/77 126/714 |
| 2007/0195923 A1 * | 8/2007 | Netsch | G06T 11/005 378/4 |
| 2008/0077005 A1 * | 3/2008 | Piron | A61B 5/0035 600/411 |
| 2008/0262240 A1 * | 10/2008 | Kibar | B03C 7/026 548/229 |
| 2008/0277567 A1 * | 11/2008 | Doran | G01N 21/4795 250/227.2 |
| 2008/0285827 A1 * | 11/2008 | Meyer | G06T 11/005 382/131 |
| 2009/0081775 A1 | 3/2009 | Hodneland | |
| 2009/0143685 A1 * | 6/2009 | Elner | A61B 5/7275 600/476 |
| 2010/0158373 A1 | 6/2010 | Li | |
| 2012/0145926 A1 | 6/2012 | Seibel et al. | |
| 2012/0231533 A1 | 9/2012 | Holl | |
| 2012/0301913 A1 | 11/2012 | Youngbull | |
| 2013/0026050 A1 | 1/2013 | Harding | |
| 2013/0075276 A1 | 3/2013 | Haoshi | |
| 2013/0280752 A1 * | 10/2013 | Ozcan | G01B 9/02047 435/29 |
| 2013/0321822 A1 * | 12/2013 | Vogler | A61B 5/0066 356/497 |
| 2014/0085623 A1 | 3/2014 | Lorbeer et al. | |
| 2015/0037827 A1 | 2/2015 | Dastoor | |
| 2015/0087007 A1 | 3/2015 | Meldrum | |
| 2015/0253333 A1 | 9/2015 | Tian | |
| 2016/0084750 A1 * | 3/2016 | Wang | G02B 21/32 435/30 |
| 2016/0202247 A1 | 7/2016 | Tian | |
| 2016/0215254 A1 | 7/2016 | Meldrum | |
| 2018/0318835 A1 | 11/2018 | Martineau | |
| 2019/0126275 A1 | 5/2019 | Kelbauskas | |
| 2019/0153005 A1 | 5/2019 | Kong | |
| 2019/0177784 A1 | 6/2019 | Martineau | |
| 2019/0276881 A1 * | 9/2019 | Zhuang | G01N 1/36 |

FOREIGN PATENT DOCUMENTS

| | | |
|---|---|---|
| WO | 2010062654 A2 | 6/2010 |
| WO | 2012112440 A2 | 8/2012 |
| WO | 2015048009 A1 | 4/2015 |
| WO | 2017083817 A1 | 5/2017 |
| WO | 2017087473 A1 | 5/2017 |
| WO | 2017151978 A1 | 9/2017 |
| WO | 2017184998 A1 | 10/2017 |
| WO | 2018013948 A1 | 1/2018 |
| WO | 2018136794 A1 | 7/2018 |
| WO | 2018157064 A1 | 8/2018 |
| WO | 2018160998 A1 | 9/2018 |
| WO | 2018213269 A1 | 11/2018 |
| WO | 2019046452 A1 | 3/2019 |

OTHER PUBLICATIONS

Wang et al., "Rotation of Cells and Cell Clusters in Culture Media for Optical Computed Tomography", Oct. 2013, Center for Biosignatures Discovery Automation, Biodesign Institute, Arizona State University, 17th International Conference on Miniaturized Systems for Chemistry and Life Sciences, 27-31.*

Arridge, "Optical tomography in medical imaging," Inverse Problems, vol. 15, pp. R41-R93, 1999.

Aubert et al, "A Variational Approach to Removing Multiplicative Noise," SIAM Journal on Applied Mathematics, vol. 68, pp. 925-946, 2008.

Bölke, T., et al. "Data-adaptive image-denoising for detecting and quantifying nanoparticle entry in mucosal tissues through intravital 2-photon microscopy." Beilstein journal of nanotechnology 5.1 (2014): 2016-2025.

Boulos, R. E., et al. Structural organization of human replication timing domains. FEBS letters 589, 2944-2957, doi:10.1016/j.febslet. 2015.04.015 (2015).

Carlton, et al, "Fast live simultaneous multiwavelength four-dimensional optical microscopy," Proceedings of the National Academy of Sciences, vol. 107, pp. 16016-16022, 2010.

Cassidy-Stone, A. et al. Chemical inhibition of the mitochondrial division dynamin reveals its role in Bax/Bak-dependent mitochondrial outer membrane permeabilization. Dev Cell 14, 193-204, doi:10. 1016/j.devcel.2007.11.019 (2008).

Cheddad, A., et al. Image processing assisted algorithms for optical projection tomography. IEEE Trans Med Imaging 31, 1-15, doi:10. 1109/TMI.2011.2161590 (2012).

Chen, B. C. et al. Lattice light-sheet microscopy: imaging molecules to embryos at high spatiotemporal resolution. Science 346, 1257998, doi:10.1126/science.1257998 (2014).

Coe R. L. et al., "Computational modeling of optical projection tomographic microscopy using the finite difference time domain method," Journal of the Optical Society of America A, vol. 29, pp. 2696-2707, 2012.

Colberg-Poley, A. M. et al. Superresolution imaging of viral protein Iralficking. Med Microbiol Immunol 204, 449-460, doi:10.1007/s00430-015-0395-0 (2015).

Dabov, et al., "BM3D ImageDenoising with Shape-Adaptive Principal Component Analysis," inProc. Signal Processing with Adaptive Sparse Structured Representation, SPARS'09, 2009.

Fauver, M. et al. Three-dimensional imaging of single isolated cell nuclei using optical projection tomography. Opt Express 13, 4210-4223 (2005).

Furlan-Magaril, M., et al. 3D genome architecture from populations to single cells. Curr Opin Genet Dev 31, 36-41, doi:10.1016/j.gde. 2015.04.004 (2015).

Gorkin, D. U., et al. The 3D genome in transcriptional regulation and pluripotency. Cell Stem Cell 14, 762-775, doi:10.1016/j.stem. 2014.05.017 (2014).

(56) References Cited

OTHER PUBLICATIONS

Gustafsson, M. G. L., et al. Structured-illumination microscopy of living cells. Abstr Pap Am Chem S 238 (2009).
Gustafsson, M. G. Surpassing the lateral resolution limit by a factor of two using structured illumination microscopy. J Microsc 198, 82-87 (2000).
Haralick, R. M., et al. Textural Features for Image Classification, Ieee T Syst Man Cyb Smc3, 610-621, doi:Doi 10.1109/Tsmc.1973.4309314 (1973).
Hell, S. W., et al. Far-field fluorescence microscopy with three-dimensional resolution in the 100-nm range. J Microsc 187, 1-7 (1997).
Hensel, M., et al. Imaging the invisible: resolving cellular microcompartments by superresolution microscopy techniques. Biological chemistry 394, 1097-1113, doi:10.1515/hsz-2012-0324 (2013).
Herman, G. T., et al. Fully three-dimensional reconstruction from data collected on concentric cubes in Fourier space: implementation and a sample application to MRI. Phys Med Biol 37, 673-687 (1992).
Huang, B., et al. Super-resolution fluorescence microscopy. Annu Rev Biochem 78, 993-1016, doi:10.1146/annurev.biochem.77.061906.092014 (2009).
Huisken, J., et al. Optical sectioning deep inside live embryos by selective plane illumination microscopy. Science 305, 1007-1009, doi:10.1126/science.1100035 (2004).
International Searching Authority, International Search Report and Written Opinion for application PCT/US2017/020528, dated Jun. 29, 2017.
International Searching Authority, International Search Report and Written Opinion for application PCT/US2018/020711, dated May 15, 2018.
Sermann, P. et al. Nuclear mechanics and mechanotransduction in health and disease. Curr Biol 23, R1113-1121, doi:10.1016/j.cub.2013.11.009 (2013).
Junttila, M. R. et al. Influence of tumour micro-environment heterogeneity on therapeutic response. Nature 501, 346-354, doi:10.1038/nature12626 (2013).
Kelbauskas, et al., "Optical computed tomography for spatially isotropic four-dimensional imaging of live single cells," Science Advances, 2017; 3: e1602580.
Kervrann C, et al. 2006. Optimal spatial adaptation for patch-based image denoising. IEEE Transactions on Image Processing 15:2866-2878. doi: 10.1109/TIP.2006.877529.
Kervrann. (2009). Software—SAFIR-nD—image denoising software[Report]. Available: http://raweb.inria.fr/rapportsactivite/RA2009/vistas/uid28.html.
Kumar, A. et al. Dual-view plane illumination microscopy for rapid and spatially isotropic imaging. Nat Protoc 9, 2555-2573, doi:10.1038/nprot.2014.172 (2014).
Le Saux, B., et al. "Isotropic high-resolution three-dimensional confocal micro-rotation imaging for non-adherent living cells." J. Microsc 233.3 (2009): 404-416.
Lindquist, S. The heat-shock response. Annu Rev Biochem 55, 1151-1191, doi:10.1146/annurev.bi.55.070186.005443 (1986).
Lucocq, J. M., et al. Systems biology in 3D space—enter the morpheme. Trends Cell Biol 25, 59-64, doi:10.1016/j.tcb.2014.09.008 (2015).
Martinez, F., et al. Structural and functional changes in mitochondria associated with trophoblast differentiation: methods to isolate enriched preparations of syncytiotrophoblast mitochondria. Endocrinology 138, 2172-2183, doi:10.1210/endo.138.5.5133 (1997).
Massague, J. et al. Metastatic colonization by circulating tumour cells. Nature 529, 298-306, doi:10.1038/nature17038 (2016).

Mayer, M. P. Gymnastics of molecular chaperones. Mol Cell 39, 321-331, doi:10.1016/j.molcel.2010.07.012 (2010).
Meyer, et al, "Automated cell analysis in 2D and 3D: A comparative study," Pattern Recognition, vol. 42, pp. 141-146, 2009.
Meyer, M. G. et al. The Cell-CT 3-dimensional cell imaging technology platform enables the detection of lung cancer using the noninvasive LuCED sputum test. Cancer Cytopathol 123, 512-523, doi:10.1002/cncy.21576 (2015).
Muller, C. B. et al. Image scanning microscopy. Phys Rev Lett 104, 198101, doi:10.1103/PhysRevLett.104.198101 (2010).
Muller, T. et al. A 3-D microelectrode system for handling and caging single cells and particles. Biosens Bioelectron 14, 247-256, doi:Doi 10.1016/S0956-5663(99)00006-8 (1999).
Neumann, T. et al. Simultaneous 3D imaging of morphology and nanoparticle distribution in single cells with the Cell-CT technology. Conf Proc IEEE Eng Med Biol Soc 2008, 379-381, doi:10.1109/IEMBS.2008.4649169 (2008).
Nunez, E., et al. Nuclear organization in the 3D space of the nucleus—cause or consequence? Curr Opin Genet Dev 19, 424-436, doi:10.1016/j.gde.2009.07.005 (2009).
Otsu, "A Threshold Selection Method from Gray-Level Histograms," IEEE Transactions on Systems, Man and Cybernetics, vol. 9, pp. 62-66, 1979.
Reichle, C., et al. Electro-rotation in octopole micro cages. J Phys D Appl Phys 32, 2128-2135, doi:Doi 10.1088/0022-3727/32/16/323 (1999).
Renaud, O., et al. "High-resolution 3-D imaging of living cells in suspension using confocal axial tomography." Biotechnology Journal: Healthcare Nutrition Technology 3.1 (2008): 53-62.
Revelo, N. H. et al. Application of STED microscopy to cell biology questions. Methods in molecular biology 1251, 213-230, doi:10.1007/978-1-4939-2080-8_12 (2015).
Shao, L. et al. I5S: wide-field light microscopy with 100-nm-scale resolution in three dimensions. Biophysical journal 94, 4971-4983, doi:10.1529/biophysj.107.120352 (2008).
Sorensen, J. G., et al. The evolutionary and ecological role of heat shock proteins. Ecology Letters 6, 1025-1037, doi:10.1046/j.1461-0248.2003.00528.x (2003).
Tokunaga, M., et al. Highly inclined thin illumination enables clear single-molecule imaging in cells. Nat Methods 5, 159-161, doi:10.1038/nmeth1171 (2008).
Tonnesen, J. et al. Two-color STED imaging of synapses in living brain slices. Methods in molecular biology 950, 65-80, doi:10.1007/978-1-62703-137-0_5 (2013).
Shetty, R.M., "Single Cell Rotation," Thesis, Approved Jun. 2013, Arizona State University.
Verveer, P. J. et al. High-resolution three-dimensional imaging of large specimens with light sheet-based microscopy. Nat Methods 4, 311-313, doi:10.1038/nmeth1017 (2007).
Weissleder, R. et al. Advancing biomedical imaging. Proc Natl Acad Sci U S A 112, 14424-14428, doi:10.1073/pnas.1508524112 (2015).
Wendt, K. S. et al. Transcription in the context of the 3D nucleus. Curr Opin Genet Dev 25, 62-67, doi:10.1016/j.gde.2013.11.020 (2014).
Wu, Y. C. et al. Spatially isotropic four-dimensional imaging with dual-view plane illumination microscopy. Nature biotechnology 31, 1032-+, Doi 10.1038/Nbt.2713 (2013).
Zhong, H. Applying superresolution localization-based microscopy to neurons. Synapse 69, 283-294, doi:10.1002/syn.21806 (2015).
U.S. Appl. No. 15/774,558.
U.S. Appl. No. 15/774,563.
U.S. Appl. No. 16/479,373.
U.S. Appl. No. 16/479,729.
U.S. Appl. No. 16/487,535.
U.S. Appl. No. 16/611,799.

\* cited by examiner

I)

J)

LIVE-CELL COMPUTED TOMOGRAPHY

CROSS-REFERENCE TO RELATED APPLICATION

CROSS-REFERENCE TO RELATED APPLICATIONS

This application represents the U.S. National Stage entry of International Application PCT/US2017/020528, filed on Mar. 2, 2017, which claims priority to U.S. Provisional Patent Application No. 62/302,649 filed on Mar. 2, 2016, the disclosures of which are incorporated herein by reference.

TECHNICAL FIELD

This present application relates to a computed tomography technology, more particularly, to computed tomography technology applied to a live or fixed cell, multicellular cluster, or tissue in suspension in the fields of clinical medicine and biological research.

BACKGROUND

Live cell imaging has advanced significantly and the field has propelled into the next cycle of application-driven developments for addressing cell biology questions that were previously unapproachable. Understanding the internal organization of biological cells, inherently 3D structures, is pivotal for the analysis of cellular function and response to external stimuli and stress. Despite the significant advances in 3D imaging of live cells, only a few methods offer nearly isotropic 3D spatial resolution. Furthermore, the majority of these imaging modalities require the cell to be immobilized during imaging, which may compromise biological dynamics when imaging natural suspension cells, e.g. immune system cells. The cellular microenvironment has been shown to be crucial for cell function, homeostasis and pathogenesis. Consequently, studies focusing on the immune system that rely on artificial immobilization of cells on substrates may alter cellular organization and affect signaling pathways, since the natural state of these cells is in liquid suspension or non-adherent in tissues.

While X-ray tomography has been in clinical use since the 1970s, optical tomography at the cellular level is relatively new. There is a need for technologies that image cell structure and function in three dimensions with true isotropic resolution (e.g., for detecting many diseases including cancer, drug screening, and in elucidating basic biological mechanisms).

SUMMARY

In one or more embodiments, provided herein is a Live-Cell Computed Tomography (LCCT) system that samples and images an individual live cell, individual fixed cell, live multicellular clusters, fixed multicellular clusters, live tissue, or fixed tissue in suspension in a module that can be attached to a commercial inverted microscope. While the cell(s) (or cluster(s)) or tissue is/are rotated "free in medium" by one of several means, or rotated in a biocompatible gel in a capillary, image projections or other transmission or emission data are acquired from a plurality of angular perspectives by an objective lens-camera combination. A three dimensional image with isotropic spatial resolution of the cell is synthesized or reconstructed by means of a series of computer algorithms, producing quantitative biosignatures useful for disease diagnosis, drug screening, and biological studies.

Embodiments of the technology disclosed herein include an optical computed tomography system for acquiring three dimensional (3D) images. The system comprises a frame having a first plane comprising a first axis and a second plane comprising a second axis, wherein the first plane is substantially orthogonal to the second plane and the first axis is substantially orthogonal to the second axis; a device manifold supported by said frame and disposed parallel to said first plane; and a first optical train connected to said frame and disposed along said second axis. Further, in certain embodiments, the system comprises a second optical train connected to said frame and disposed along said second axis. Moreover, in certain embodiments, the system further comprises a scanning objective, a camera, and a light delivery module.

In certain embodiments, the frame further comprises a platform that is able to move along the first axis, the second axis, and a third axis, wherein the third axis is disposed with the first plane and is substantially transverse to the first axis. The device manifold further comprises a microfluidic module configured to comprise an object rotation region and at least one imaging chamber. Moreover, the device manifold further comprises an object dispensing region, which comprises a fluid pumping apparatus comprising an air pressure controller, a vacuum controller, a fluid reservoir, and a flow monitoring device.

Embodiments of the technology disclosed herein also include a method of rotating an object. The method comprises generating a rotating electric field; inducing an electric dipole moment in the object by the rotating electric field; and rotating the object at a speed by the rotating electric field. In certain embodiments, the object is selected from the group consisting of a live cell, live multicellular cluster, fixed cell, fixed multicellular cluster, live tissue, fixed tissue, and any combinations thereof.

In addition, embodiments of the technology disclosed herein include a method of creating a 3D image of acquiring a 3D image of an object. The method comprises rotating the object to complete a 360 degree rotation; acquiring a two dimensional (2D) pseudo-projection image of the object during rotation to form a plurality of M 2D pseudo-projection images of the object; and constructing a 3D image of the object based on said plurality of 2D pseudo-projection images of the object.

BRIEF DESCRIPTION OF THE DRAWINGS

The technology disclosed herein will be better understood from a reading of the following detailed description taken in conjunction with the drawings in which like reference designators are used to designate like elements, and in which.

DETAILED DESCRIPTION

The present application is directed to systems and methods of using the same for capturing a functional fluorescence 3D image of a cell, multicellular cluster, or tissue in suspension, more particularly, a live cell, multicellular cluster, or tissue with isotropic 3D diffraction-limited spatial resolution. Optical computed tomography (CT) imaging of a single cell(s) (and cell cluster(s) and tissue) is made possible by recent developments in low-light level imaging and other detectors, microelectronics, microfluidics and high-speed computing.

This technology disclosed herein is described in one or more exemplary embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the technology disclosed herein. Thus, appearances of the phrases "in one embodiment," "in an embodiment," and similar language throughout this specification may, but do not necessarily, all refer to the same embodiment.

The described features, structures, or characteristics of the technology disclosed herein may be combined in any suitable manner in one or more embodiments. In the following description, numerous specific details are recited to provide a thorough understanding of embodiments of the technology disclosed herein. One skilled in the relevant art will recognize, however, that the technology disclosed herein may be practiced without one or more of the specific details, or with other methods, components, materials, and so forth. In other instances, well-known structures, materials, or operations are not shown or described in detail to avoid obscuring aspects of the technology disclosed herein.

Figure 11:
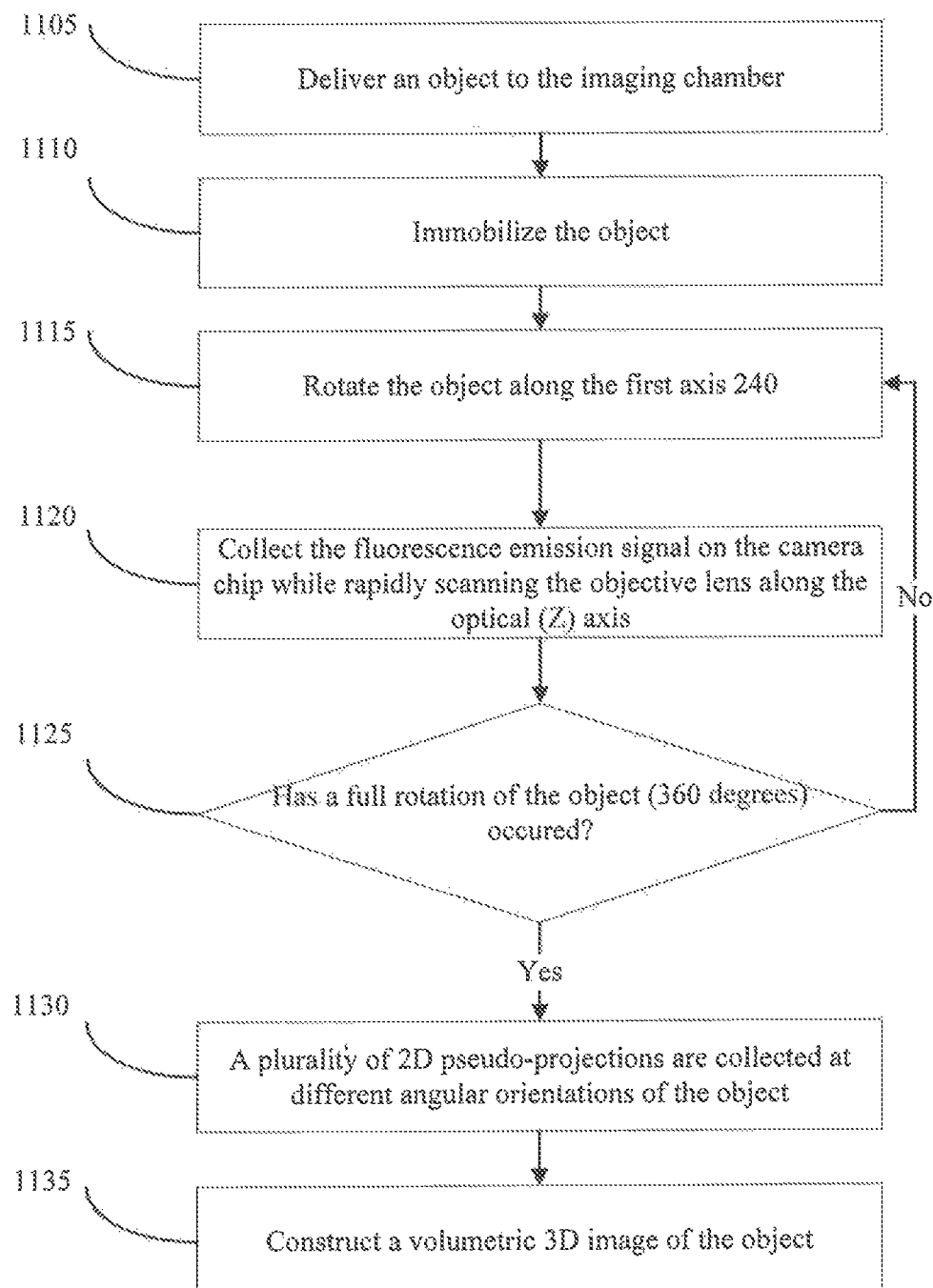
FIG. 11 is a flowchart illustrating one embodiment of the method of acquiring a plurality of 2D images of an object and constructing a 3D image based on the plurality of the 2D images.

The schematic flow chart diagrams included are generally set forth as a logical flow-chart diagram (e.g., FIG. 11). As such, the depicted order and labeled steps are indicative of one embodiment of the presented method. In certain embodiments, other steps and methods are conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types are employed in the flow-chart diagrams, they are understood not to limit the scope of the corresponding method (e.g., FIG. 11). Indeed, some arrows or other connectors may be used to indicate only the logical flow of the method. For instance, an arrow indicates a waiting or monitoring period of unspecified duration between enumerated steps of the depicted method. Additionally, the order in which a particular method occurs may or may not strictly adhere to the order of the corresponding steps shown.

As used herein, "electric dipole moment" is defined as a measure of the separation of positive and negative electrical charges within a system, that is, a measure of the system's overall polarity. The electric field strength of the dipole is proportional to the magnitude of dipole moment. The SI units for electric dipole moment are Coulomb-meter (C m), however the most commonly used unit is the Debye (D). An electric dipole is defined by the first-order term of the multipole expansion, and consists of two equal and opposite charges infinitely close together.

"Spatial resolution" refers to the number of pixels utilized in construction of a digital image. Images having higher spatial resolution are composed with a greater number of pixels than those of lower spatial resolution. This interactive tutorial explores variations in digital image spatial resolution, and how these values affect the final appearance of the image.

"Point spread function (PSF)" describes the response of an imaging system to a point source or point object. A more general term for the PSF is a system's impulse response, the PSF being the impulse response of a focused optical system. The PSF in many contexts can be thought of as the extended blob in an image that represents an unresolved object. In functional terms it is the spatial domain version of the transfer function of the imaging system.

"Temporal resolution" refers to the precision of a measurement with respect to time. Often there is a trade-off between the temporal resolution of a measurement and its spatial resolution, due to Heisenberg's uncertainty principle.

Figure 1:
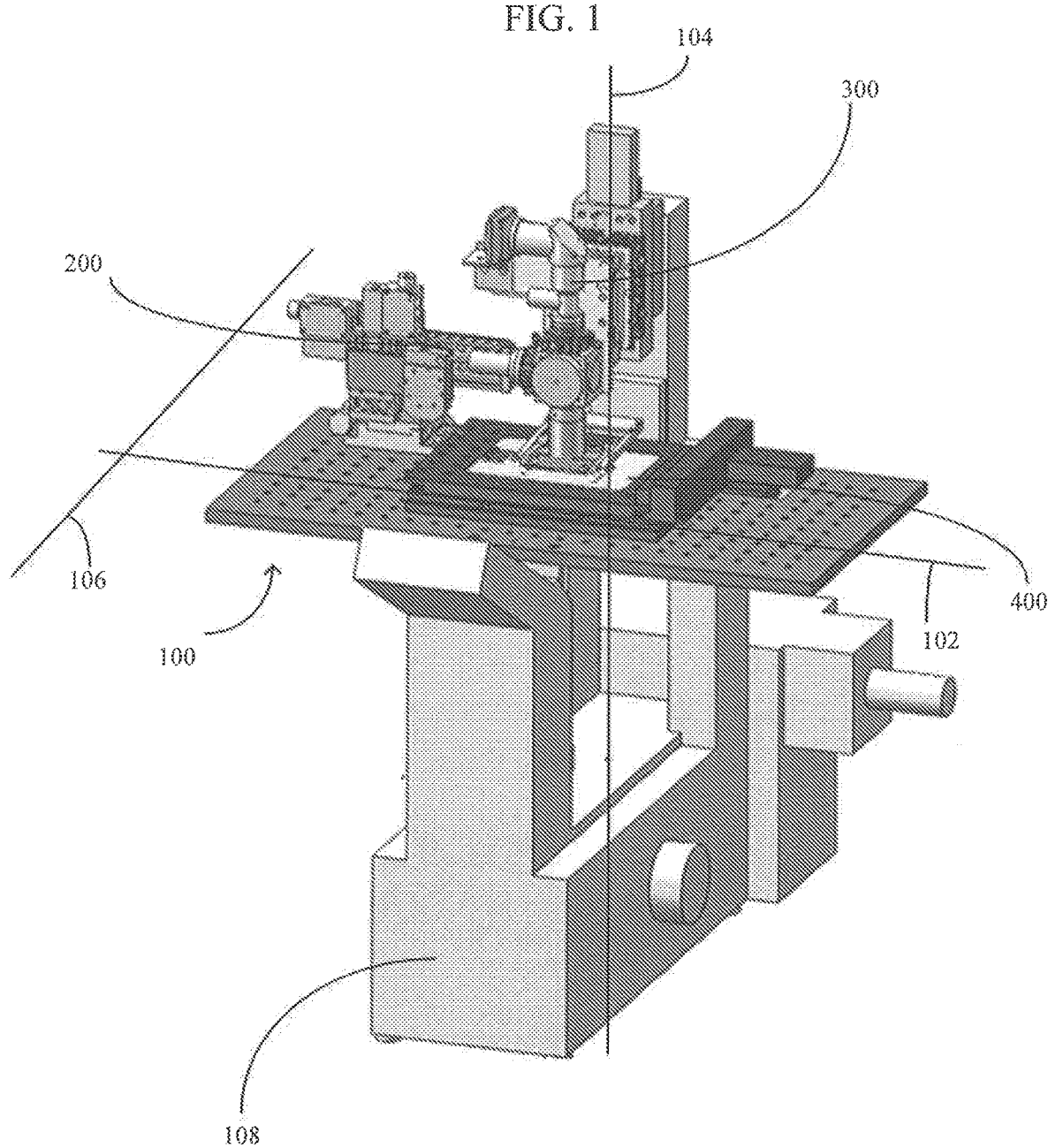
FIG. 1 illustrates one embodiment of a Live-Cell Computed Tomography (LCCT) instrument frame with three major subcomponents shown.

Referring to FIG. 1, an embodiment of the Live-Cell Computed Tomography (LCCT) system is illustrated. In certain embodiments, the LCCT system 100 is built around a frame, which is a microscope as shown in FIG. 1. In certain embodiments, the frame 108 comprises three major physical subcomponents: a first (primary) optical train 200, a second (secondary) optical train 300, and a device manifold 400. In other embodiments, the frame 108 comprises the first optical train 200 and the device manifold 400. Further, the frame 108 comprises a first plane comprising a first axis 102 and a second plane comprising a second axis 104. Moreover, the first plane comprises a third axis 106, which is substantially transverse to the first axis 102.

Figure 2:
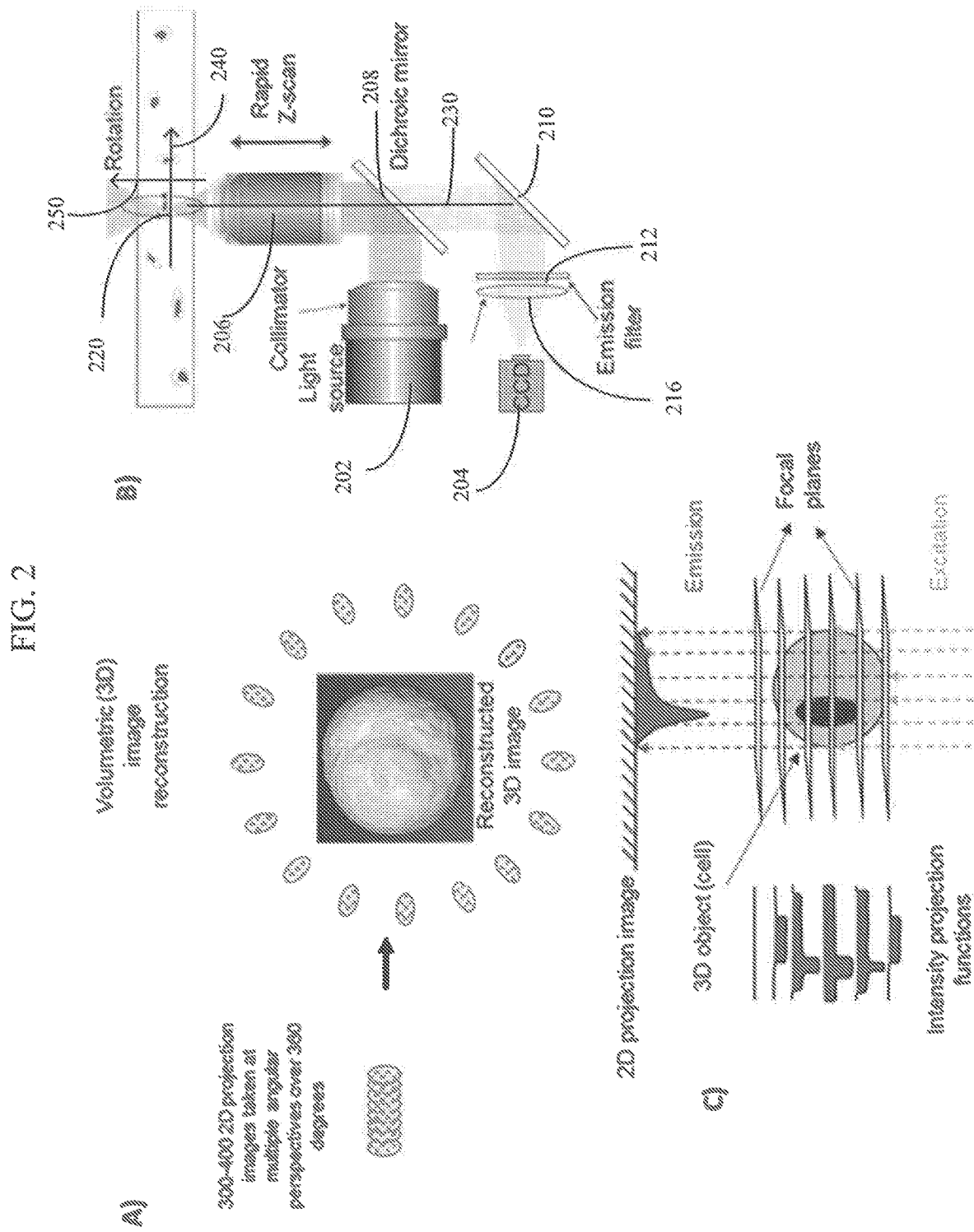
FIG. 2A depicts volumetric 3D image reconstruction.
FIG. 2B illustrates one embodiment of a primary optical train schematic
FIG. 2C depicts a 2D pseudo-projection image.

Referring to FIG. 2B, an embodiment of the first optical train 200 is illustrated. In certain embodiments, a light source 202 delivers a light via an internal optical path to a first dichroic mirror 208, which reflects the light to a scanning objective 206 along an optical axis 230. In some embodiments, the light source 202 delivers a laser light. In other embodiment, the light source 202 comprises a light-emitting diode (LED), which is a two-lead semiconductor light source and emits light when activated. The scanning objective 206 can focuses on an object 220. In some embodiments, the object 220 is a single live cell or a single fixed cell. In other embodiments, the object 220 is a live or fixed multicellular cluster(s). In other embodiments, the object 220 is a live or fixed tissue. In yet other embodiments, the object 220 is a microparticle amenable to imaging with visible optical radiation.

Further, an emission signal generated by the object 220 travels along the optical axis 230 through the scanning objective 206 to a second dichroic mirror 210, which reflects the emission signal to a emission filter 212 onto a camera chip 216. The emission signal can be captured by a camera 214. In some embodiments, the camera 214 is an electron-multiplying charge-coupled device (EMCCD). In other embodiments, the camera 214 is a scientific complementary metal-oxide-semiconductor (sCMOS) camera.

Figure 3A:
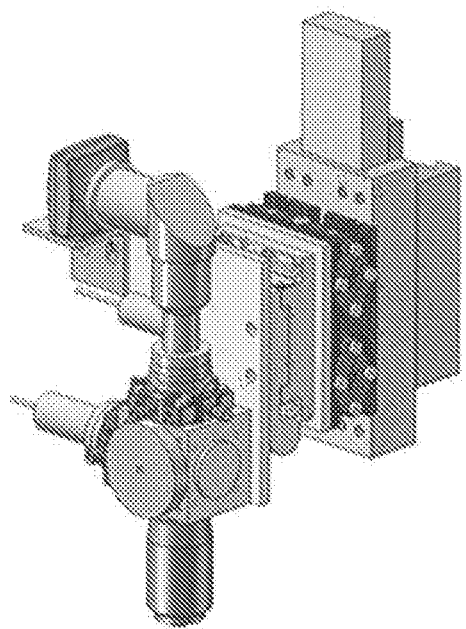
FIGS. 3A and 3B illustrates one embodiment of a secondary optical train schematic and model.
Figure 3B:
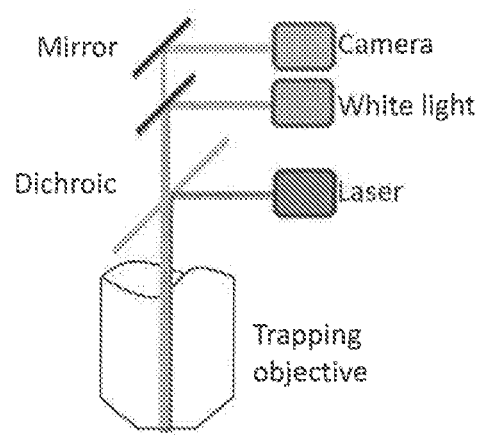

Referring to FIGS. 3A and 3B, one embodiment of a secondary optical train 300 is illustrated. In some embodiments, the secondary optical train 300 is used for transmission mode imaging. In other embodiments, the secondary optical train 300 is used for optical trapping of the cells. In certain embodiments, the basic components of the secondary optical train 300 are similar to the first optical train 200, however the assembly is mounted directly opposite the primary optical train and on the same optical axis 230 (FIG. 2B). The secondary optical train 300 serves to deliver or receive transmitted light to and/or from the object 220. Referring to FIG. 3B, a laser beam delivered through a light source can act as an optical trap to confine or immobilize the object 220 for imaging.

Figure 4:
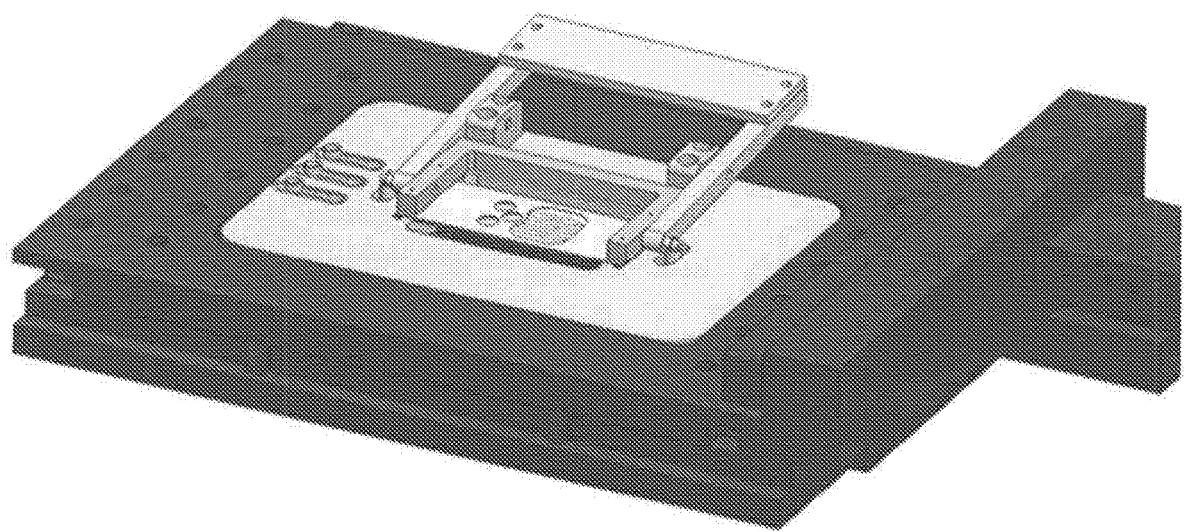
FIG. 4 illustrates one embodiment of a device manifold.

Referring to FIG. 4, one embodiment of the device manifold 400 is illustrated. In certain embodiment, the device manifold 400 comprises a microfluidic module, which contains an object rotation region, or "imaging chamber". In some embodiments, the device manifold 400 comprises one or at least one imaging chamber. In other embodiments, the device manifold 400 comprises a plurality of imaging chambers. In certain embodiments, the device manifold 400 further connects to at least one of a fluid driving system, light delivery modules, computers and other appendages.

Further, the device manifold 400 is mounted to an X-Y-Z motion platform in order to bring the object cell(s) precisely into the field of view. The device manifold allows for a simple loading and unloading of a microfluidic device which incorporates the imaging chamber. Moreover, the device manifold 400 interfaces fluid and electrical inputs between the system 100 and the microfluidic device. The device manifold 400 can have the ability to hold additional parts. As a non-limiting example, a series of PCR tubes can be hold by the device manifold 400.

Figure 5:
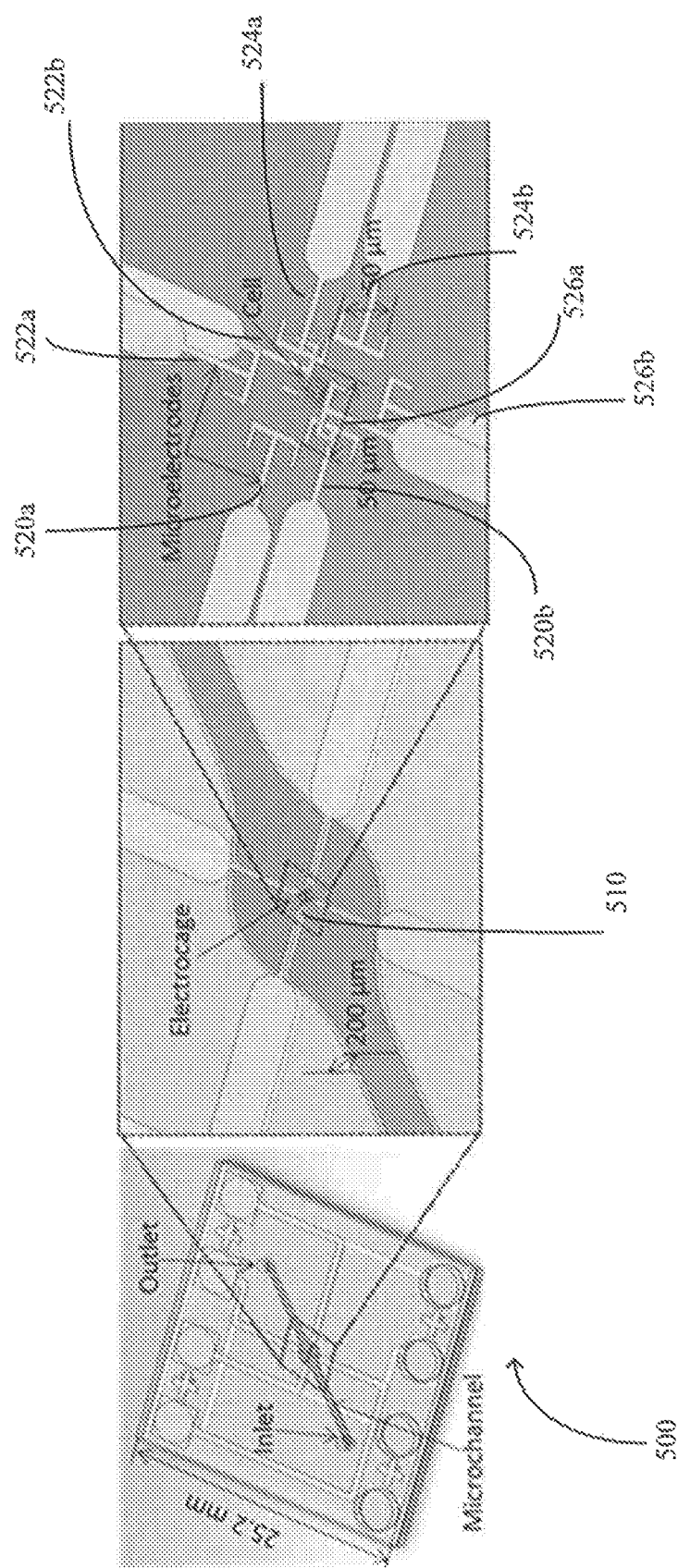
FIG. 5 illustrates one embodiment of cell rotation.

The microfluidic device can be manufactured to effect any of several cellular rotation methods. Three methods of rotation are based upon: asymmetrical light pattern, hydrodynamic vortex, and dielectrophoretic torque ("electrocage"). Referring to FIG. 5, an embodiment of the microfluidic device 500 facilitates an electrocage 510 for rotating the object 220.

Furthermore, the microfluidic device incorporates means for delivering the object 220 to the optical axis 230 of the microscope. All methods may use fluid flow. In addition to fluid flow, one method utilizes optical tweezers, delivered via one of the optical trains, to trap the object 220 of interest and manipulate it through the microfluidic device to the optical axis 230. A second method utilizes a plurality of microelectrodes arranged along the microfluidic channel.

Referring to FIG. 11, in step 1105, the object 220 is delivered to the imaging chamber 500. In certain embodiments, a polysaccharide cell medium can be used to suspend the object 220 and support its life and normal function as it is delivered to the optical axis 230 and then rotated. In step 1110, the object 220 is immobilized. Further, in step 1115, the object 220 is rotated steadily along a first axis 240 of an electric field. The first axis 240 is substantially transverse to the optical axis 230.

Figure 6:
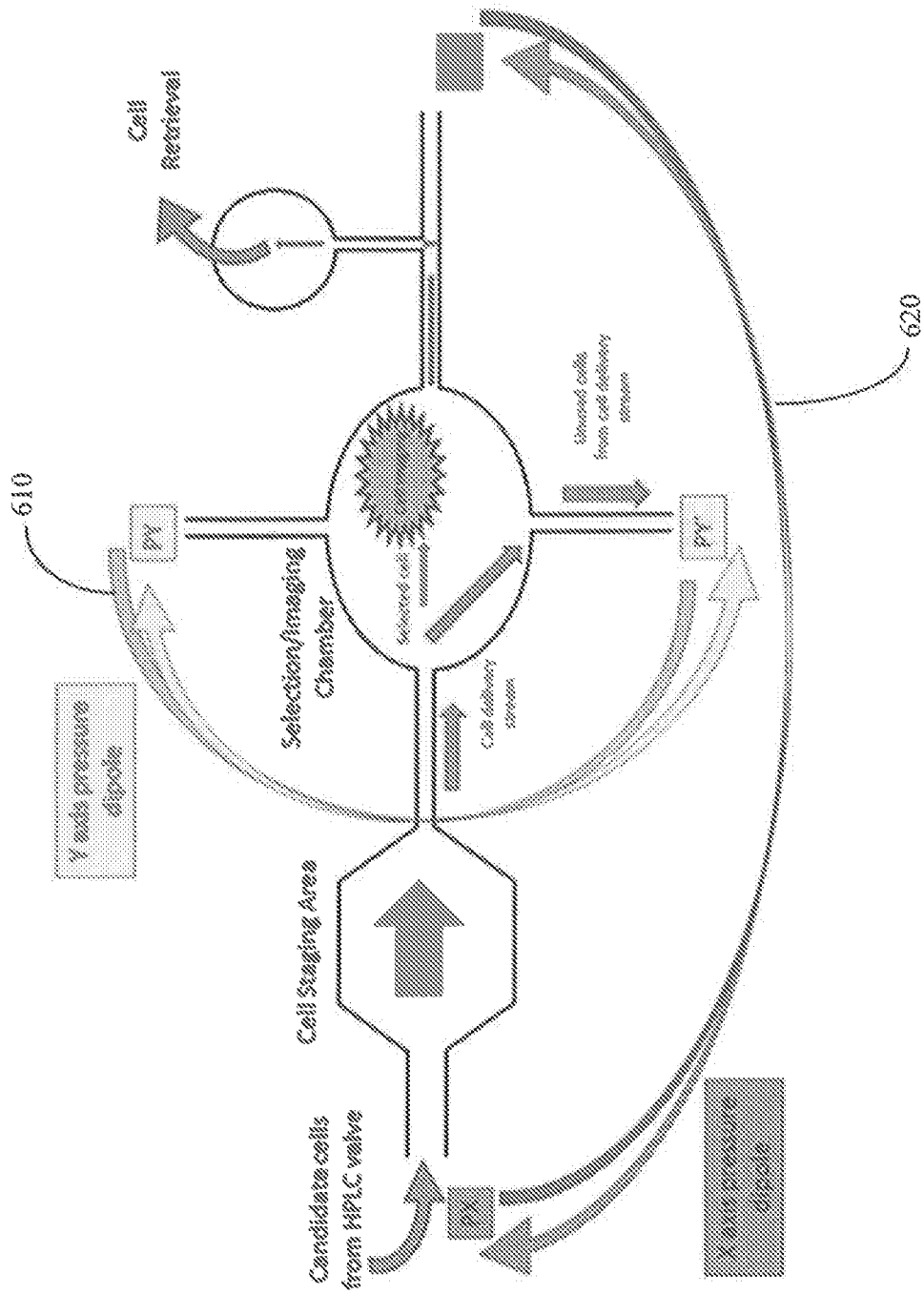
FIG. 6 illustrates one embodiment of delivering an object from a cell staging area to an imaging chamber in a fluid manner.

Referring to FIG. 5, the imaging chamber 500 comprises a plurality of microelectrodes 520a, 520b, 522a, 522b, 524a, 524b, 562a, and 526b. Microelectrodes 520a, 522a, 524a, and 526a are located within one plane, which is directly above the other plane, within which microelectrodes 520b, 522b, 524b, and 526b are located. The electric current following through all the microelectrodes generates an electric field 510, which can also be called the electrocage. The electric field 510 further comprises a y-axis dipole 610 (FIG. 6). Also, the electric field 510 comprises an x-axis dipole 620 (FIG. 6), which cause the object 220 to rotate along the x-axis. The electric field 510 is a high frequency electric field with a rotating phase pattern in the 3D space. The cell rotation is a result of an induced dipole moment in the cell due to the rotation of the electric field that imposes a torque on the cell.

Moreover, in certain embodiments, the rotating electric field pattern is generated by applying a sinusoidal waveform at a frequency of 1-10 megahertz (MHz) and voltage (V) peak-to-peak amplitude to each of the microelectrodes with a phase offset by 90 degrees. In other embodiments, the sinusoidal waveform has a frequency of 1-2 MHz and 1-2 V peak-to-peak amplitude to each of the microelectrodes. In yet other embodiments, the electrical field frequency is about 0.5-2 MHz and the electrical field amplitude is about 2 V (peak-to-peak). In certain embodiments, using the electrocage 510, Applicants are able to consistently rotate live myelogenous leukemia cells (K562 cell line) and mouse macrophages (J774A.1 cell line) at stable speeds ranging between 1-3 rotations per minute (RPM). In other embodiments, the cell rotation speed is about 1-10 rotations per minute (RPM), e.g., 1.5 RPM, 2 RPM, 2.5 RPM, 3 RPM, 3.5 RPM, 4 RPM, 4.5 RPM, 5 RPM, 5.5 RPM, 6 RPM, 6.5 RPM, 7 RPM, 7.5 RPM, 8 RPM, 8.5 RPM, 9 RPM, 9.5 RPM, 10 RPM, or another RPM from about 1 to about 10 RPM. As described herein, "about" is defined as plus or minus 10% difference in any measurement.

Figure 7A:
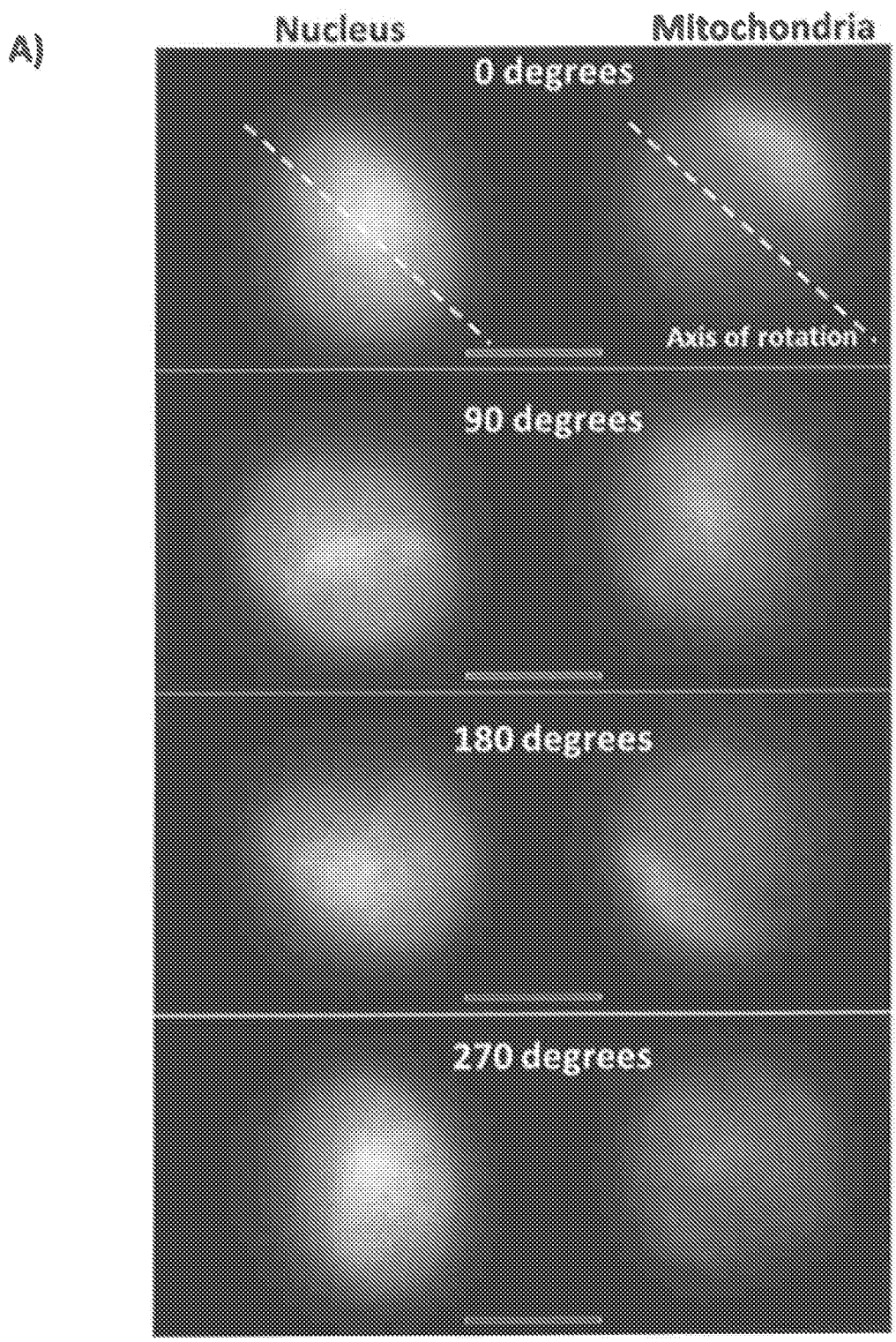
FIG. 7A shows that projection images obtained at four orientations of the cell during a full rotation in the electrocage device, Scale bar: 5 microns.
Figures 7B, 7C, 7D, 7E, 7F:
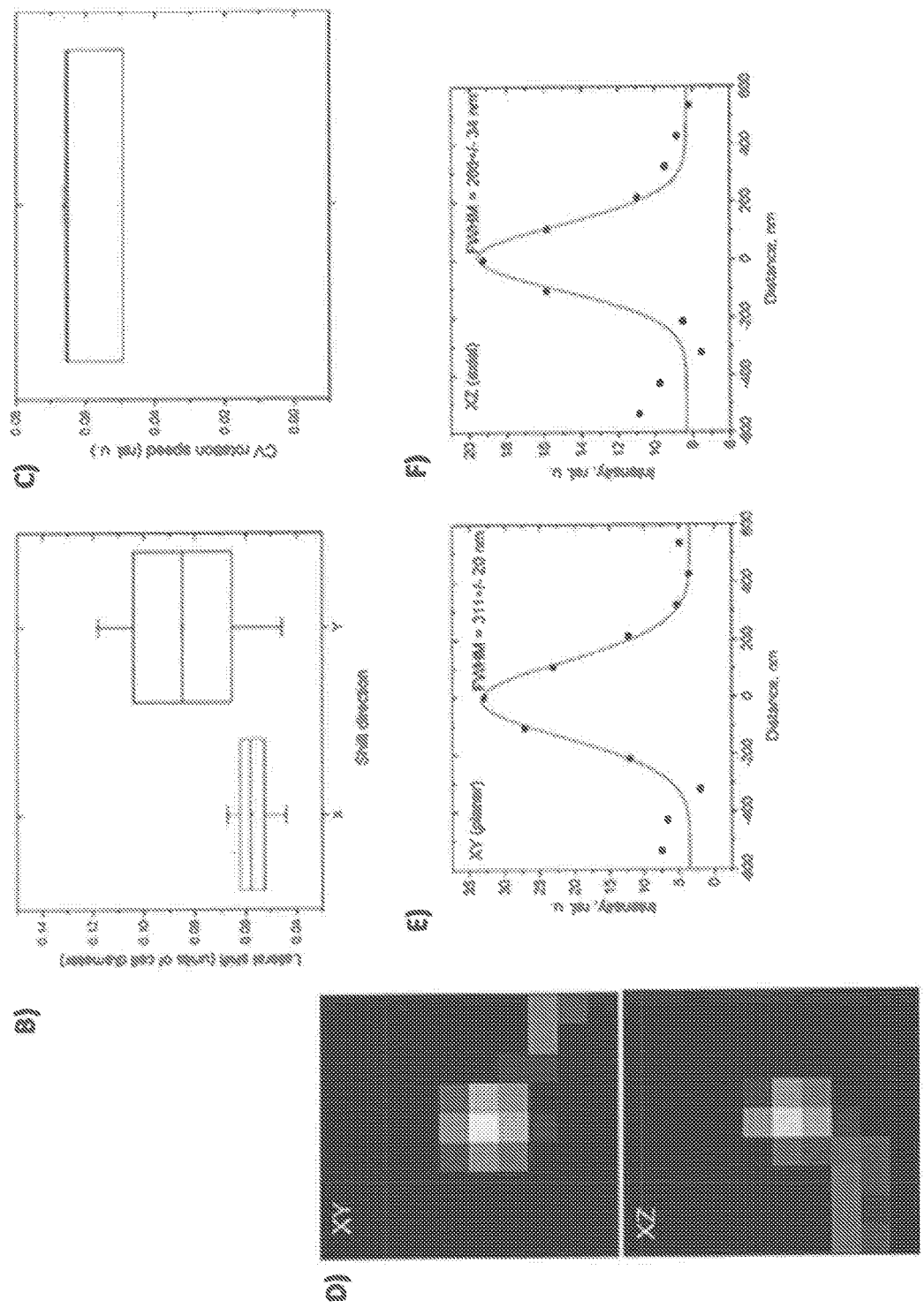
FIGS. 7B and 7C show lateral shift of the cell along X and Y axis during one full rotation and rotation rate stability.
FIG. 7D shows spatial resolution characterization using 200 nm fluorescent beads. Beads were internalized by the cells prior to experiment. Images of one such bead are shown in XY and XZ direction.
FIGS. 7E and 7F shows lateral spatial resolution.

In addition, rotation stability of the object 220 is characterized by measuring lateral, in-plane shifts in the X and Y direction during a full 360° rotation of the object 220. While the lateral displacement of cells varied from cell to cell, it appeared to depend on the cell shape (or how far it deviated from an ideal spherical shape). Image analysis revealed a coefficient of variation, or relative lateral shift, from the initial (0°) cell position of 0.057 and 0.084 of the cell diameter in X and Y directions per full rotation of the cell, respectively (FIG. 7B). Such shifts take place over an entire rotation of the cell (20-60 seconds) and are relatively slow when compared with the time scale of an individual, one direction/half cycle scan pseudo-projection acquisition (40 ms). Consequently, adjusted to the 40 ms time scale these shifts can be ignored, as they become minor, resulting only in about $10^{-4}$ shift of the cell diameter (assuming 2 RPM or 30 seconds/rotation, online Materials and Methods) and do not distort pseudo-projection images appreciably. As a result, lateral shifts on this time and spatial scale can be reliably corrected computationally, using appropriate algorithms.

To fully characterize cell rotation stability, Applicants determined how stable the rotation rate is over multiple rotations of the same cell. To this end, we calculated the coefficient of variation of the rotation rate using data of five cells with 5-7 full rotations each (FIG. 7C) We find that the average coefficient of variation of the rotation rate per full rotation is 0.051. Similar to the argument presented for the lateral shift, this results in $7 \cdot 10^{-5}$ average variation in rotation rate per single pseudo-projection and does not appreciably affect data collection. For a vast majority of the studied cells (~95% of cells), the orientation of the rotation axis of the cell remained stable during rotation. Cells that exhibited slight, but appreciable wobbling were excluded from analysis.

In certain embodiments, a hydrodynamic vortex rotation method can be used to rotate the object 220. For this method, a fluid pumping system may be needed. The pumping system may consist of a low (positive) air pressure controller and low vacuum controller. These controllers are upstream of a fluid reservoir filled with deionized water. The reservoir leads to a flow monitoring device that creates a feedback loop for software control of the pressure controllers; it is in this manner that minute fluid flow rates are obtained, with exquisite flow control. The pumping system may incorporate a (cell solution) sample loading loop or other valving downstream of the flow monitor device and upstream of the tomograph device manifold 400.

Referring to FIG. 11 again, following step 1115, in step 1120, the fluorescence emission signal of the object 220 is collected on the camera chip 216 (FIG. 2B) while rapidly scanning objective lens located within the scanning objective 206 along the optical axis 230 over a range that is large enough to interrogate the entire object 220 (FIG. 2B). In certain embodiments, the object 220 is fluorescently labeled by internalizing a plurality of fluorescent beads into the object. Further, in certain embodiments, the scanning objectives 206 can traverse up and down through a continuum of focal planes, by means of, for example, a piezo motion device, collecting data at a continuum of planes through the object 220. The emission signals emanating from the whole object 220 can be integrated by the camera chip during each of such scans effectively producing the mathematical equivalent of a projection that one would obtain with a parallel beam (FIG. 2C). In certain embodiments, a spatial, high-frequency band-pass filter should be used on each projection image to remove the accumulated low-frequency background.

In step 1125, whether a full rotation of the object 220 (360 degrees) has occurred need to be determined. Once a full rotation has occurred, the method transitions to step 1130, wherein a plurality of 2D pseudo-projections are collected. In certain embodiments, about 300 projections are collected over a full rotation (360 degrees) at an angular sampling rate of 1.2. degrees. In other embodiments, about 500 projections are collected over a full rotation (360 degrees) at an angular sampling rate of 0.72 degrees. In yet other embodiments, any suitable angular sampling rate between about 0.72 degrees and about 1.2 degrees can be utilized and a corresponding number of projections will be collected over a full rotation (360 degrees). A volumetric (3D) image of the cell is then reconstructed using computational algorithms in step 1135. If a full rotation has not occurred yet, the method transitions to step 1115 and the method will repeat step 1115 and 1120 until a full rotation of the object 220 completes.

When a cell(s) is delivered to the imaging chamber, immobilized and optionally rotated, the objective lens-detector combination may be used to acquire fluorescence (emission), transmitted (absorption), reflected or scattered optical radiation from the object. The collected data is submitted to and processed by computer algorithms to form images, including three-dimensional images, of the object cell. In some embodiments, if the collected data is transmitted or emitted projections of the object 220 at a multiplicity of angles, such data may be submitted for processing by computed tomography algorithms similar to those evoked in radiological X-ray CT. In other embodiments, structural or functional images or other representations of the object 220 can be produced from the acquired, processed data without the use of CT reconstruction algorithms.

This is advantageous for poorly immobilized cells or for cells rotating about an unstable rotation axis. The quantitative images and image analyses automatically produce quantitative biosignatures that can be used, for example, for disease diagnoses and mechanistic studies of biological processes.

An additional functionality of this instrument is its ability to collect the object 220 after optical data (image) acquisition, and deliver the object 220 to a destination container for downstream experiments. The device for this function is shown in FIG. 6. As an example, the device may employ a high precision fluidic pump to collect the object 220 from the tomographic microfluidic device, then deposit the object 220 into a tube (e.g., PCR tube) for the purposes of genomic, transcriptomic, proteomic or other biomolecular analyses. An alternate implementation of end-point analyses is to perform the genomic, transcriptomic, and/or proteomic analyses of the object 220 while they remain inside the tomographic microfluidic device. The microfluidic device already has the ability to introduce other reagents needed for molecular analyses. The microfluidic chip within the microfluidic device can be placed on a thermal plate for any required thermal processing.

While one or more exemplary embodiments of the technology disclosed herein have been illustrated in detail, it should be apparent that modifications and adaptations to those embodiments may occur to one skilled in the art without departing from the scope of the present disclosure.

Methods

Electrocage Microfabrication

In one or more embodiments, the fabrication of the electrorotation chip may require the bonding of two separate chips (180 µm, and 500 µm), with four electrodes each, in order to form an octopole for cell rotation.

Following the fabrication of the individual dies, the final chip for cell rotation is assembled. The 180 µm die with the micropatterned fluidic channel is used as the bottom half of the chip for imaging with high spatial resolution. The two dies are aligned on a mask aligner stage for precision control, and are bonded by wicking in an ultraviolet (UV) adhesive via capillary forces. Once the microchannel has been completely surrounded by the UV adhesive, it is cured under UV-light which creates a permanent seal around the perimeter of the chip. The electrical connections to the waveform generator are made on a custom PCB board with preexisting contacts. This approach enables convenient handling of the electrocage chip, which sits snugly on this fixture during experiments. There are two fluidic connections. A fluidic probe connected to a 50 µL syringe for precise manual control of fluid in the chip creates a removable, sealed contact with one port of the microfluidic channel on the chip. A pipette tip or nanoport is glued to the other fluidic port and provides an inlet for introducing cells.

Cell Culture and Fluorescent Staining

K562 cells (human chronic myelogenous leukemia cells) were cultured in RPMI 1640 medium (Gibco, Grand Island, N.Y., USA) containing 10% fetal bovine serum (Gibco, Grand Island, N.Y.), 100 units mL-1 penicillin, and 100 µg mL-1 streptomycin at 37° C. in a humidified incubator containing 5% CO2. The cell density was determined using a Countess® II FL Automated Cell Counter (Life Technologies, Grand Island, N.Y.). Cultures were maintained by the addition or replacement of fresh medium. J774A.1 cells (mouse macrophage cells) were cultured in Dulbecco's Modified Eagle's Medium supplemented with 10% fetal bovine serum (Gibco, Grand Island, N.Y., USA), 100 units mL-1 penicillin, and 100 µg mL-1 streptomycin at 37° C. in a humidified incubator containing 5% CO2. Subcultures were prepared by scraping a 75 cm$^2$ flask, removing all but 10 mL of the culture medium. The volume was adjusted accordingly for different culture vessels. The cell density was determined using the automated cell counter. The nucleus and mitochondria of K562 and J774A.1 cells were stained simultaneously using Hoechst 33342 (H3570, Life Technologies, Grand Island, N.Y.) and MitoTracker Red (M-7512, Life Technologies). For staining, 3 µL 0.5 µM Hoechst 33342 and 3 µL 1 µM MitoTracker Red into a 1 mL 1 million cell sample was added and incubated for 30 minutes.

Live Cells with Beads Samples

To characterize spatial resolution of the system, we combined 200 nm diameter beads (Life Technologies) with live K562 cells and imaged the cells with LCCT. To make the live cell and beads sample, 1 mL of cell medium containing 10$^6$ K562 cells were put into a PCR tube and mixed with 0.3 µL of bead stock. The sample was incubated for 4 hours to make sure the beads were taken up by the cells. After 4 hours, the sample was centrifuged at 500 g for 7 minutes to form a pellet, the supernatant was aspirated and pellet re-suspended in 1 mL of fresh cell culture media. The centrifugation step was repeated twice to remove any remaining free beads in the media.

Effects of Electrocage Parameters on Cell Rotation Rate

The magnitude of the dielectrophoretic (DEP) force is proportional to the gradient of the electric field, which is generated by the voltage applied to the microelectrodes. Therefore, an appropriate starting voltage should be chosen for experiments. The experiments were set up with a frequency fixed at 2 MHz, and were done on a chip with a 50 µm spacing between the two electrode layers. The diameter of the tested human myelogenous leukemia cells (K562 cell line) was 18±3 µm. A graph of the number of K562 cells successfully rotated as a function of voltage applied is shown. Based on this result we chose the amplitude value of 2 V (peak-to-peak) as a good starting point to perform electrorotation.

It is known that the frequency of the electric field is closely related to rotational parameters like speed, and rotational direction. In order to determine the relation between different frequencies and the cell rotation rate, the voltage amplitude was fixed at 2 V while the frequency was adjusted from 0.2 to 7 MHz. The cell size, and chip electrode gap were the same as for the previous voltage amplitude study. As expected, we observed an increase in the rotation rate with increasing electric field frequency. A slow rotation rate, of 1-2 RPM is desirable for collecting a large number of pseudo-projections during one full rotation of the cell. The number of collected pseudo-projection images directly affects spatial resolution and SNR of the reconstructed volumetric images. Therefore, a working frequency range of 0.5-2 MHz was chosen as best suited for imaging. Lower frequencies were avoided as they may induce ionic currents leading to cell stress and membrane electroporation, while we observed that higher frequencies can lead to cell membrane damage.

Rotational Stability Characterization

We observed two types of distortions of an ideal rotation in the electrocage that can affect the quality of 3D image reconstruction from 2D pseudo-projection images: 1. Lateral shift in the XY plane of the cell, and 2. Alterations in rotation rate. We determined average lateral shifts along the X and Y axes during a full rotation of the cell to be 0.057 and 0.084 in units of cell diameter. Assuming a 10 µm diameter of a typical cell, the average lateral shifts are 0.57 µm and 0.84 µm per full rotation of the cell. Our typical rotation rates are in the range of 1-3 rotations per minute (RPM) or 20-60 seconds/rotation. We calculate the average lateral shift per each individual pseudo-projection as follows:

$$s_{ave} = S_{ave} \times \frac{t_{exp}}{T_{rot}}$$

where $S_{ave}$ is the average lateral shift along one axis per full rotation, $t_{exp}$ is the exposure time for individual pseudo-projection image acquisition, and $T_{rot}$ is the rotation period. Assuming a 30 second rotation period and given the average lateral shifts along the X and Y axis of 0.57 µm and 0.84 µm, respectively, and the exposure time of 40 ms, we calculate save values of 0.76 nm and 1.12 nm for X and Y axis, respectively.

Our cell stability measurement yielded an average rotation rate instability of 5.1% per full rotation. Assuming a typical rotation rate of 2 RPM (30 second rotation period), this translates into an absolute average instability of 0.1 RPM per full rotation. By analogy with the lateral shift calculation consideration, we define the average rotational rate error per individual pseudo-projection using the following equation:

$$r_{ave} = R_{ave} \times \frac{t_{exp}}{T_{rot}}$$

where $R_{ave}$ is the average deviation of the rotation rate in RPM, $t_{exp}$ is the exposure time for individual pseudo-projection image acquisition, and $T_{rot}$ is the rotation period. Given $t_{exp}=0.04$ s, $R_{ave}=0.1$ RPM, and assuming a $T_{rot}=30$ s, we calculate a rotation rate instability per pseudo-projection $r_{ave}=0.00013$ RPM.

We note that both types of instabilities—lateral shift and rotation rate instability—are small and do not affect the image quality of pseudo-projections appreciably in terms of introducing movement artifacts.

In addition to the deviations in lateral position and rotation rate of the cell, the fact that the cell rotates continuously during pseudo-projection acquisition should be considered. Consequently, one needs to determine the amount of blurring that will occur due to the cell movement and how it may affect image quality. To this end we determine the upper limit of such distortion by calculating the distance that a pixel at the outer boundary of the cell would travel during the exposure time over which a pseudo-projection image is acquired. Using the same assumptions as above, i.e. a 10 µm cell diameter, 30 second rotation period (360 degree rotation), we calculate the angular distance of the cell during the 0.04 s exposure time for image acquisition as:

$$\alpha = 360 \times \frac{t_{exp}}{T_{rot}} = 360 \times \frac{0.04}{30} \, 0.48 \text{ degrees}$$

The distance a pixel at the outer boundary of a 10 µm diameter cell would travel is the arc length:

$$l = 2\pi r \frac{\alpha}{360} = 6.28 \times 5 \times \frac{0.48}{360} = 0.042 \text{ µm} = 42 \text{ nm}$$

where r is the cell radius. We can see that the motion blur is small compared with the spatial resolution of the system (280-290 nm at 550 nm) and can be neglected.

Assessment of Cell Stress in High Frequency Electrical Fields

To assess potentially adverse effects of exposure to a high frequency electric field on cell health we performed a series of experiment to assess cell stress. It is possible that external electric fields generated by the electrocage may induce a stress response that manifest in changes in the biomolecular profile and/or alterations in morphology of the cell. To address this question, we first designed and implemented a test platform to evaluate the stress at the bulk sample level. We used the well-understood electrical properties of a set of parallel electrodes that produce a uniform electric field E=V/d, where V is the voltage difference between the electrodes, and d is the separation between them. When the size of the electrodes is significantly larger than d, the electrical field leakage at the edges is negligible. The device is composed of two 2×3" glass microscope slides with gold coating on one side, and a 50-µm-thick spacer made of adhesive non-conducting tape used in the semiconductor industry. The separation between the electrodes is the same as that in the electrocage. After cells suspended in growth medium are pipetted onto one of the electrodes, the medium is sandwiched with a second electrode and a voltage of 2 V at 2 MHz is applied across the electrodes. We selected the same alternating current waveform as that used in the electrocage, so the electrical stress between the plate electrodes can effectively simulate the actual situation during the cell rotation process in the electrocage. The presence of cellular stress was tested under five different conditions followed by western blot analysis to monitor expression levels of the heat-shock protein 70 (HSP70). We chose HSP70 as stress indicator owing to its central role in the cellular stress response and high sensitivity to a broad variety of stress types. For each stress condition, we loaded approximately 2 million cells into the uniform electrical field. A total of five conditions were tested: Condition 1: Control. Cells were kept in the incubator with no disturbance. Condition 2: Cells sandwiched between electrodes with no electrical field applied. This condition was tested to ensure there is no significant stress caused by transferring cells onto the device. Condition 3: Cells between electrodes with the electrical field applied. Condition 4: Same as in Condition 3 followed by a recovery phase at 37° C. for 4 hours. Condition 5: Conventional heat shock at 42° C. for 10 minutes as a positive control, We found no significant increase in HSP70 expression levels resulting from the exposure to the electric field (FIG. S5). In addition to the HSP70 expression levels, we performed time-lapse imaging of live K562 cells where we investigated whether a prolonged continuous exposure (>4 minutes) to electric field would induce measurable changes in cellular morphology. In line with the HSP70 findings, the imaging revealed no gross changes in cell morphology (cell size and overall intracellular organization) at sub-micron resolution during a continuous 4-5 minute rotation in the electrocage. Furthermore, turning the electric field on or off in the electrocage did not cause measurable changes in cellular morphology (data not shown). These findings suggest that the electric fields used for cell rotation in the electrocage do not cause measurable stress levels in live cells under experimental conditions used for imaging.

System Setup

One of our main goals was to design a system simple enough to be replicated and implemented in any research or clinical lab. Therefore, the system was designed around a standard, commercially available inverted microscope with epi fluorescence imaging capability. A schematic of the LCCT system, and a picture of the complete system setup is shown in FIG. S7B. We note that except for the microfluidic chip for cell rotation, all other parts are commercially available with some of them, such as the LED light source and CCD camera, already in routine use by many labs worldwide. The system comprises three main sub-systems: 1) cell rotation system; 2) epi fluorescence image acquisition system; 3) optional confocal optical imaging system for comparison purposes.

The cell rotation sub-system is composed of an integrated microfluidic chip ("electrocage") that combines a microfluidic channel and 8 microelectrodes arranged on two layers. An 8-channel computer-controlled waveform generator was used to create sinusoidal waveforms to drive the electrocage.

The image acquisition sub-system comprises an inverted microscope equipped with appropriate filters for fluorescence detection and a LED light source connected to the back port of the microscope for fluorescence excitation. A fast-scan piezo stage with an objective lens mounted on it is used to sweep the imaging plane of the objective lens through the entire cell for obtaining projection images. A dual-channel spectral module (DCSM) is attached to the right port of the microscope to split the emission photons coming from two different fluorophores into respective halves of the detector chip. Fluorescence is detected by a cooled electron-multiplying charge-coupled device (EMCCD) camera. Custom software was developed to control timing and synchronization between the cell rotation and imaging modules.

For comparison with and validation against another, already established imaging modality, we integrated a commercial confocal swept-field module onto the left port of the microscope. This capability is optional for routine CT imaging.

The system setup is built around a commercial inverted microscope (Ti-U, Nikon, Melville, N.Y.) equipped with a Xenon arc lamp (wavelength range 320 nm to 700 nm, Lambda LS, Sutter Instruments) or a multi-LED light source connected to the back port of the microscope for fluorescence excitation. A filter cube mounted in the microscope turret contains an excitation filter (Semrock, FF01-407/494/576-25) and a multichroic beamsplitter (Semrock, FF436/514/604-Di01-25x36) for selecting appropriate excitation wavelengths that are absorbed by the fluorophore and blocks other sources of light. A fast-scan piezo stage (part of the confocal swept-field module described below) with an objective lens (S Fluor, 100× oil, NA 0.5-1.3, Nikon) mounted on it is used to scan the image plane of the objective lens. An intermediate 1.5× lens mounted inside of the microscope was used to obtain a total optical magnification of 150× (100× objective lens×1.5× intermediate lens). A dual-channel spectral module (DCSM) (DV2, Photometrics, Tucson, Ariz.) is placed on the right port of the microscope to spectrally split the emission photons coming from two different fluorophores into respective halves of the detector chip. Each spectral channel is projected onto one half of a camera chip simultaneously using two emission filters (FF01-452/45-25, Semrock and ET630/75m, Chroma Technology) mounted in the DCSM. A cooled EMCCD camera (Evolve 512, Photometrics), is connected to the DCSM and is used to acquire projection images. The physical pixel size of the camera is 16 µm×16 µm resulting in an optical pixel size of 16 µm/150× magnification=0.107 µm (107 nm). The optical pixel size is below the Nyquist criterion for diffraction-limited resolution of 258 nm/2=179 nm (assuming 550 nm emission wavelength and numerical aperture of 1.3) and thus satisfies the spatial sampling requirement. An optional swept-field confocal module (SFC) (Prairie SFC, Bruker, Billerica, Mass.) is attached onto the left port of the microscope for comparison purposes. The SFC is equipped with four lasers with excitation wavelengths of 406, 488, 532, and 561 nm. The confocal image acquisition was accomplished using PrairieView v.5 software.

EXAMPLES

Example 1

Imaging Human Myelogenous Leukemia Cells

After establishing reproducible and stable cell rotation, we performed a series of imaging experiments with live K562 cells with the goal of characterizing the spatial and temporal resolution of the method. To determine spatial resolution, we used fluorescent 200 nm diameter beads internalized through endocytosis into cells as a "biological" phantom. The beads were incubated with cells at low concentration so that each cell contained on average between 3-10 beads distributed sparsely inside the cell. The cells were then rotated and imaged in the electrocage under the same conditions as in a typical experiment. Reconstructed volumetric image data were used to characterize the point spread function (PSF) of the system (FIG. 7D). We determined the spatial resolution as the full width at half maximum (FWHM) of the bead intensity profiles (FIG. 7E, F). We found a resolution in the planar (XY) direction of 311±20 nm and 280±34 nm in the axial (XZ) direction. This corresponds closely with the theoretical limit of the spatial resolution due to diffraction of 258 nm and expressed as $d=0.61\lambda/NA$, where $\lambda$ is the wavelength of the emitted light (550 nm in our case), and NA is the numerical aperture of the objective lens (1.3 in our experiments). The optical pixel size of the system is 107 nm, which satisfies the Nyquist sampling criterion of 258nm/2=179 nm for diffraction-limited spatial resolution (Online Materials and Methods). We note that despite the about 10% difference in the spatial resolution along the two directions, the difference is within the measurement error.

Our approach of using point-like emission sources such as beads inside of live cells closely replicates real imaging conditions. This strategy accounts for refraction and scattering inside the cell in contrast to the widely used method of using fluorescent beads suspended in pure aqueous solution as a calibration standard. One of the factors determining spatial resolution of our approach is the number of projection images collected during one full rotation. The higher the number of projections the denser is the spatial sampling of the object, which translates into a more accurate representation of the spatial object's data.

There are several limiting factors determining the speed at which projection images can be collected. First, the number of fluorescence photons emitted by the fluorophore molecules over a unit of time (emission intensity) and consequently the signal-to-noise ratio (SNR) of the image play a major role. One can increase the emission photon intensity by increasing excitation light intensity at the expense of increased photobleaching rate. As a result, a balance between SNR and photobleaching needs to be established. We found that we could reliably acquire projection images with an SNR of 4-10, when collecting images at a rate of 10 frames per second without causing significant photobleaching for continuous imaging over 5 minutes using the Hoechst 33343 nuclear stain. Second, in our approach the number of projections that could be collected during one full rotation was the scan speed of the objective lens (FIG. 2B). Due to considerable weight of high numerical aperture objective lenses (~300 grams), inertia becomes a limiting factor by distorting the linear part of the scan at speeds higher than 10 scans per second.

The temporal resolution of the approach was determined as the time needed to collect a full set (300-400) of projection images with high SNR to produce high quality volumetric reconstructions. To this end, we stained the nucleus and the mitochondria of K562 cells and collected projection images at rotation speeds of 1-3 RPM, which resulted in a temporal resolution of 60-20 seconds/volume, correspondingly. We note that we were able to achieve higher temporal resolution of down to ~7 seconds/volume by increasing the rotation speed and reducing the number of projections per rotation. However, the overall quality of the reconstructed volumes was reduced resulting in lower SNR.

Figure 7G:
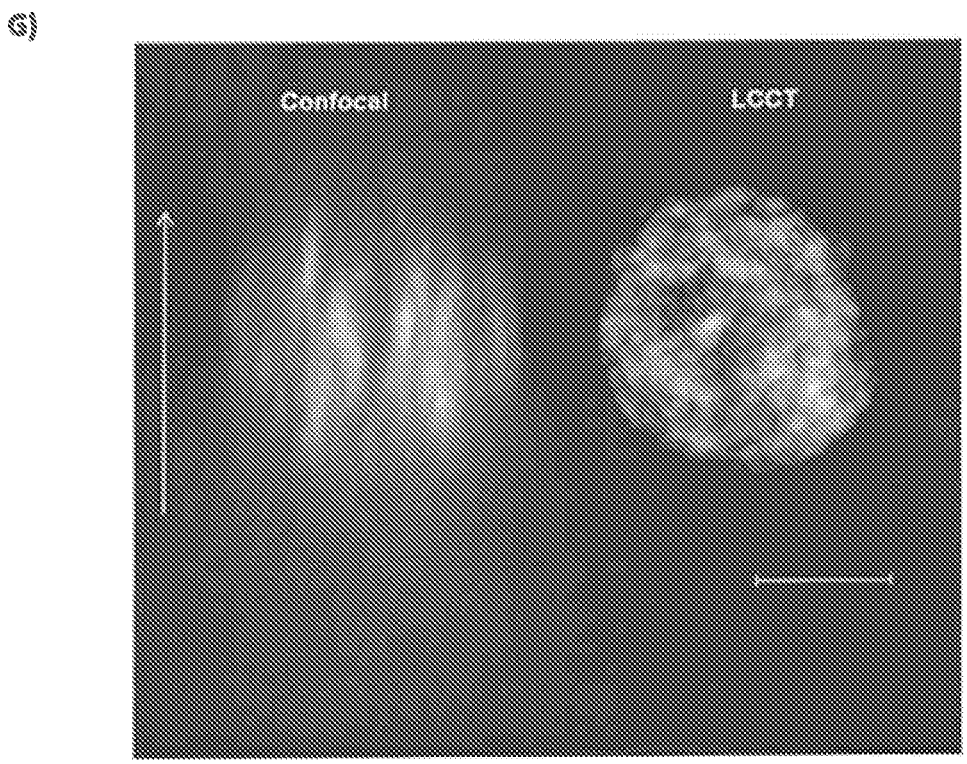
FIG. 7G demonstrates the advantage of the LCCT approach of distortion-free, orientation independent 3D imaging due to isotropic spatial resolution.

For characterization purposes, we compared 3D imaging capabilities of the LCCT approach with those of confocal imaging, which is widely used in the field of biology and biomedical research. To this end, we imaged the same cells with fluorescently labeled nuclear DNA using both imaging modalities, where we reconstructed 3D images of the nucleus from confocal Z-stacks or pseudo-projection data in case of LCCT (FIG. 7G). As expected, we found that the typical elongation of the object along the optical axis of the system due to inferior spatial resolution in confocal imaging was absent in 3D reconstructed images obtained with LCCT due to isotropic spatial resolution. This illustrates the advantage of the LCCT approach to perform orientation-independent measurements of live cells with the same spatial resolution along all three spatial directions.

A representative example of reconstructed volumetric data of a live K562 cell with fluorescently stained nucleus and mitochondria is shown in FIG. 8. The nuclear stain revealed a highly varying pattern of DNA density distribution inside the nucleus presented as maximum intensity projection (MIP) images taken at three orthogonal orientations (FIG. 8A). Furthermore, the volume rendering image (false-colored panel) shows surface textural features and a fold-like feature (FIG. 8A, arrow) with co-localized mitochondria (FIG. 8C, D). Overall, the mitochondria of the cell appear distributed in a non-random manner around the nucleus.

Figures 8A, 8B:
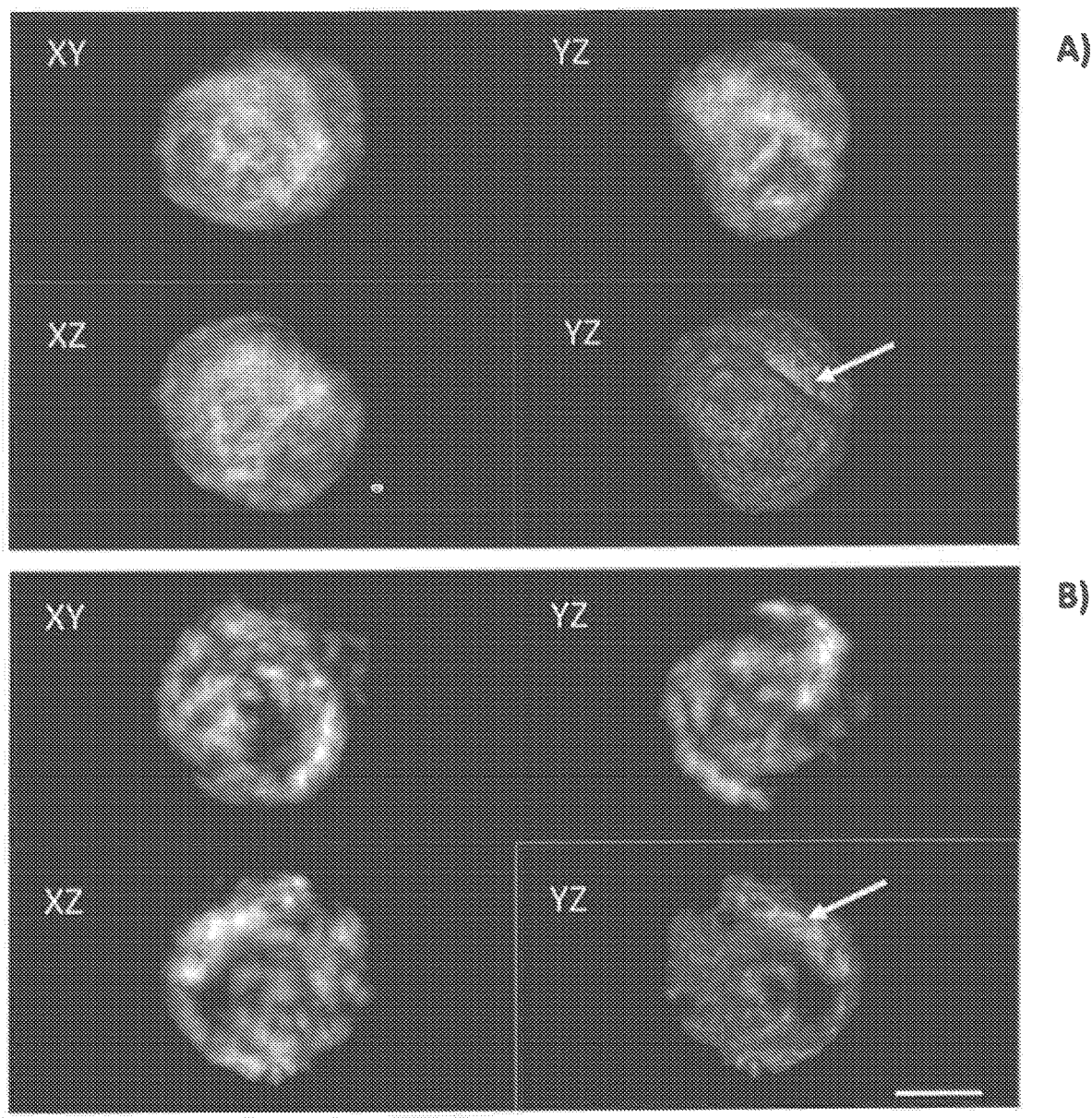
FIG. 8A illustrates MIP images at three orthogonal orientations (grayscale) and volume rendering (color, lower right) of the nuclear DNA stained with Hoechst 33342. Lighter regions in the MIP images correspond to higher density of the DNA. A fold-like feature can be seen in the volume rendering (arrow)
FIG. 8B shows MIP images of the mitochondria of the same cell as in FIG. 8A stained with the mitochondrial marker MitoTracker Red. A volume rendering (lower right panel) indicates some of the mitochondria co-localized with the fold in the nucleus in FIG. 8A.
Figure 8C:
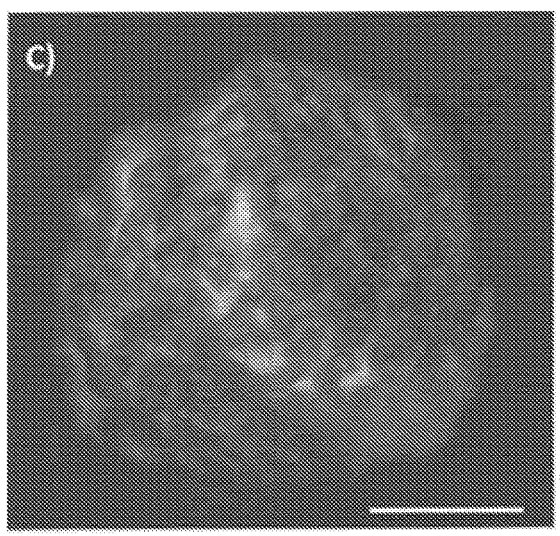
FIG. 8C is an overlay of the volume renderings of the nuclear and mitochondrial data shows some of the mitochondria (arrow) aligned with the fold in the nucleus in FIG. 8A.
Figure 8D:
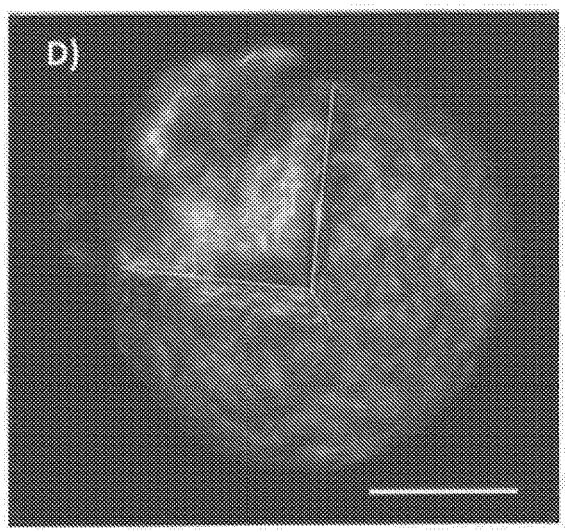
FIG. 8D is a cut-away presentation of the overlay reveals mitochondria located deep in the nuclear fold.
Figure 8E:
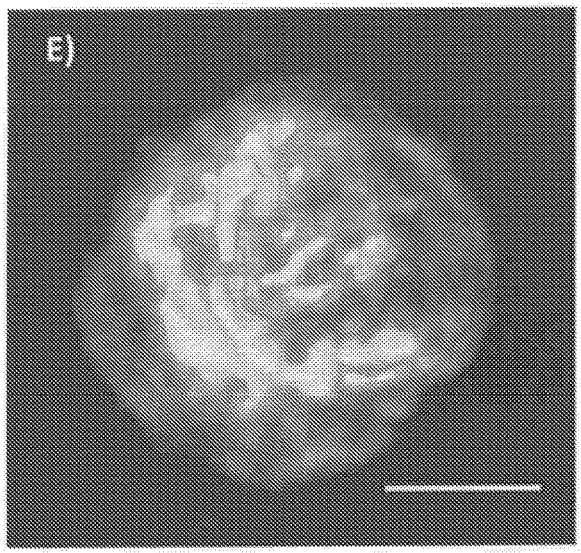
FIGS. 8E and 8F are partial segmentation of the bright (70-100% range of the intensity histogram) nuclear and mitochondrial structures, correspondingly, using an intensity threshold above 70% of the camera detection dynamic range highlights the brightest features of the two organelles. Both data sets—the nucleus and mitochondria—were acquired simultaneously. Both sets of data were deconvolved using a Gaussian point spread function. Scale bar: 5 µm.
Figure 8F:
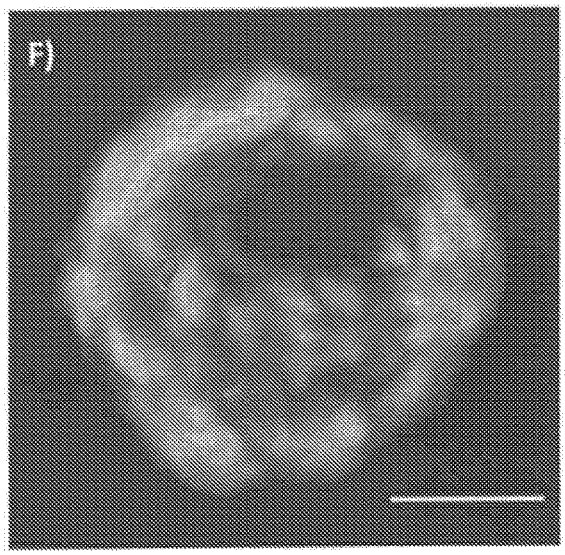
Figure 8G:
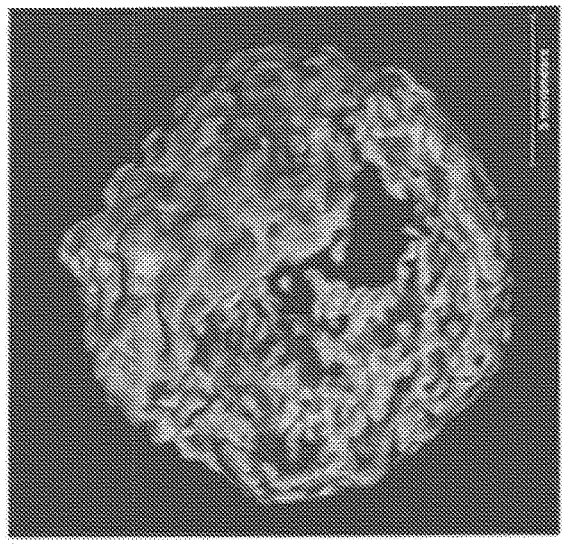
FIG. 8G shows mitochondria of the same cell presented as a series of slices through the cell at different depths (left panel). The contrast was enhanced in the intensity images to make less intense structures visible. The panel on the right shows segmentation of the mitochondria using the Niblack local threshold approach. The segmentation results were smoothed to enhance visibility. Scale bar: 5 µm.
Figure 8H:
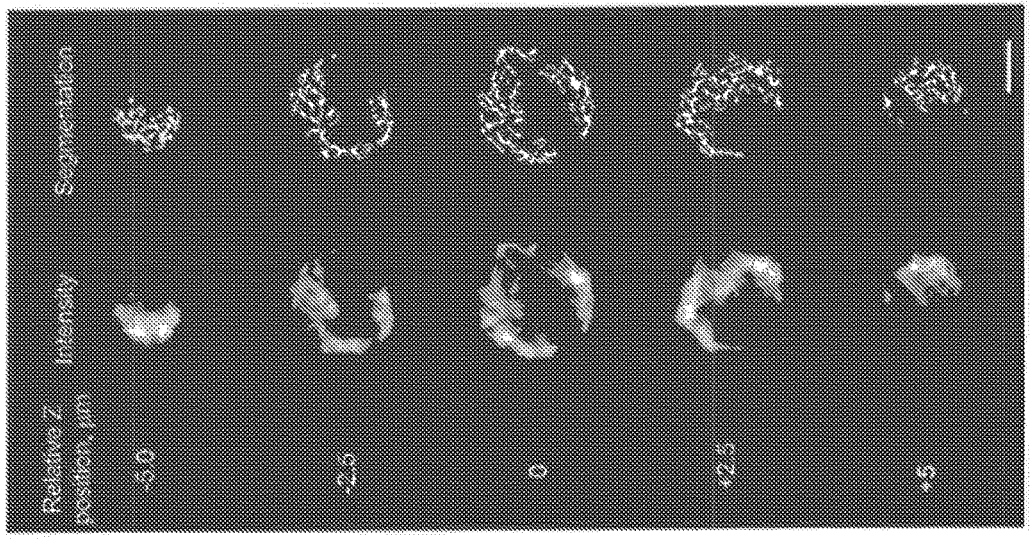
FIG. 8H is a 3D surface rendering of the mitochondrial network of the same cell with fluorescence intensity and segmented mitochondria shown in gray and orange, respectively.
Figure 8I:
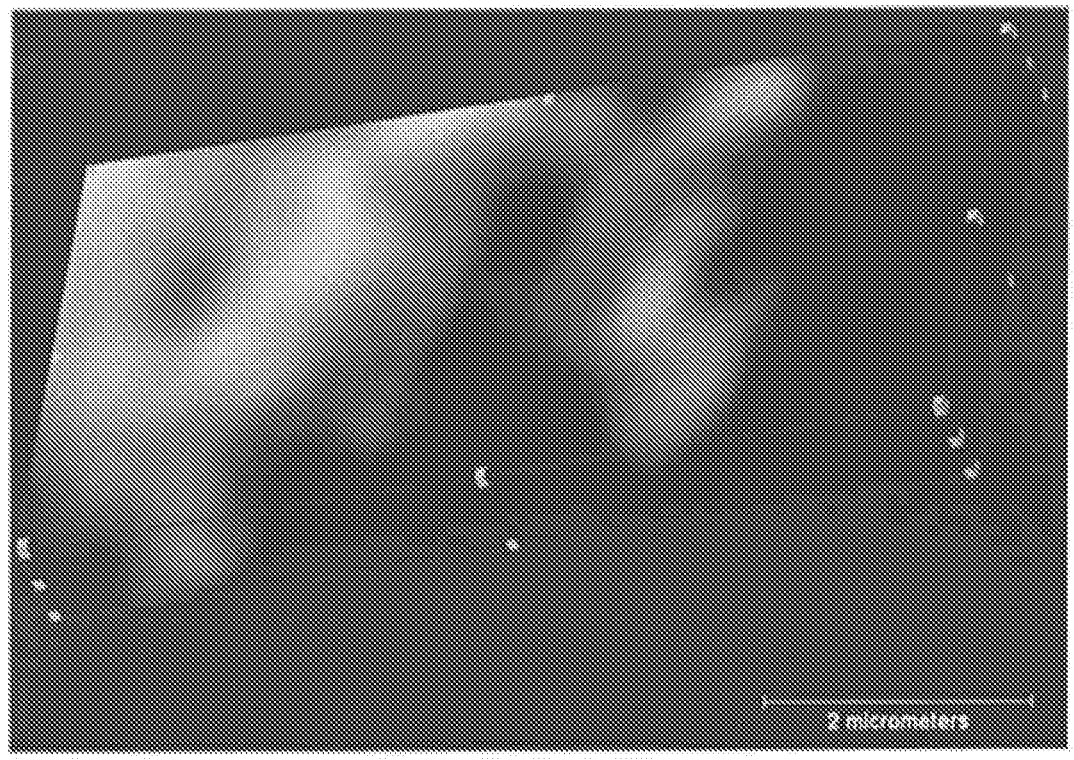
FIGS. 8I and 8J shows mitochondria fluorescence intensity (I, surface rendering) and the corresponding segmentation result (J) of a selected small region of interest of the same cell.
Figure 8J:
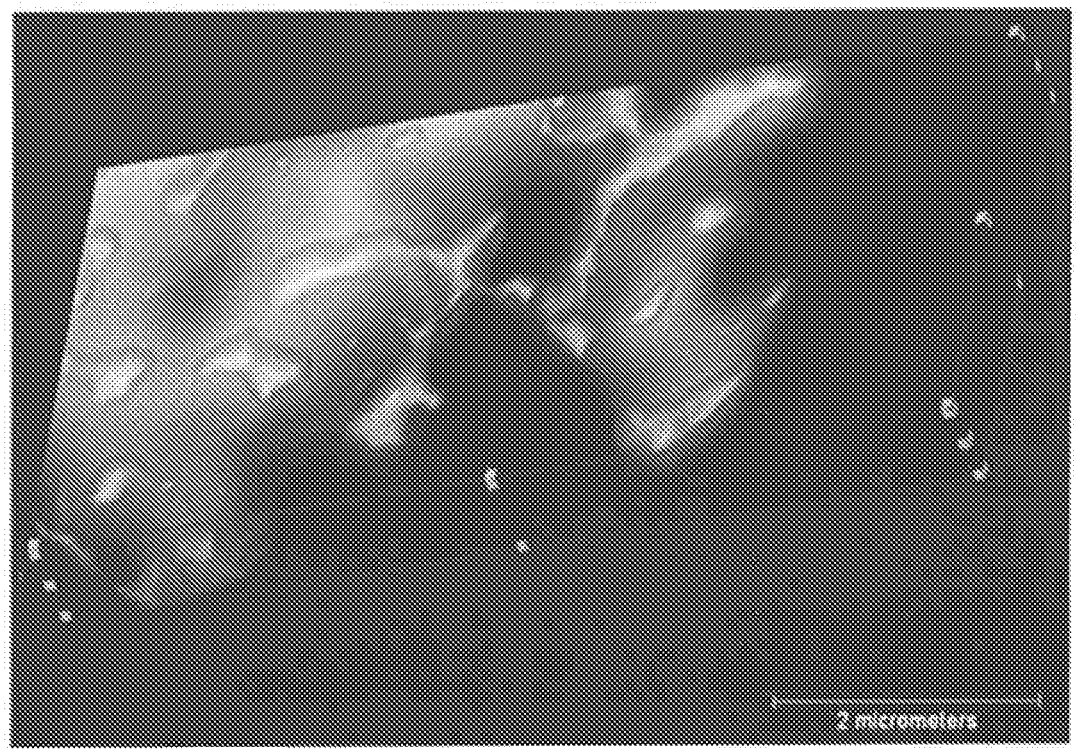

We performed feature extraction based on the intensity histogram thresholding to demonstrate the ability to obtain quantitative information about nuclear and mitochondrial structural features. FIGS. 8E and F depict segmentations of the nuclear and mitochondrial features (colored overlays on MIP images) in the upper 30% of the intensity scale, correspondingly. The rather simple segmentation illustrates how quantitative 3D spatial information (center of mass coordinates, volumes, relative positions etc.) about structural features can be extracted and analyzed. We note that while MIP images represent a good solution for presenting 3D data in 2D format, their intrinsic limitation lies in that a substantial amount of intensity detail is lost, especially when presenting densely distributed small structures with varying intensity. To illustrate the appearance of mitochondria more adequately, we show these organelles in form of slices at 5 different depths of the reconstructed 3D image along with the corresponding segmentation results (FIG. 8G).

It is possible that the mitochondrial dynamics during the collection of a full set of projection images (full cell rotation or 30 seconds) may lead to a blurred appearance of the mitochondria in volumetric images. To evaluate this aspect, we imaged mitochondria in fixed K562 cells using confocal microscopy. In both cases, the mitochondrial morphology is qualitatively similar and appears as complex, dense 3D networks distributed around the nucleus.

Example 2

Nuclear and Mitochondrial Dynamics Study

Mitochondrial Fission Inhibition

Figures 9A, 9B, 9C:
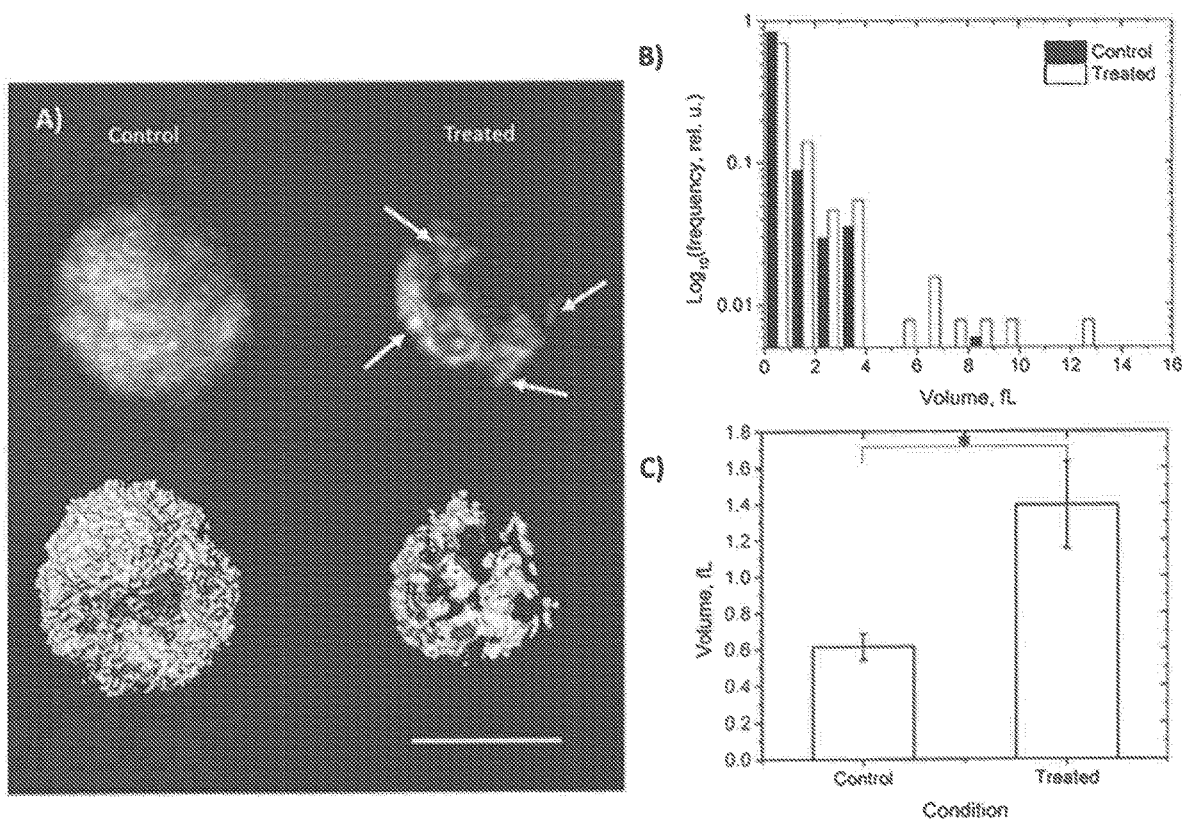
FIG. 9A is a comparison of an untreated J774A.1 cell (left) and one treated with 8-bromo-cAMP (right). MIP (upper row) and isosurface rendering (bottom row) show a marked shift towards larger structures.
FIG. 9B shows quantitative analysis of the mitochondrial structure volumes corroborate the qualitative findings of FIG. 9A showing the appearance of structures with larger volume in the treated cell.
FIG. 9C is a comparison of the average values of the volume distribution demonstrates statistically significant ($p=0.001$, Kolmogorov-Smirnov test, increase in the volume of the structures after treatment.

To validate our approach we conducted a series of experiments where we compared mitochondrial distribution characteristics in untreated naive mouse macrophages (cell line J774A.1) with macrophages treated with an inhibitor of mitochondrial dynamics. We expected to observe an increase in the mitochondrial volume resulting from treatment with validated mitochondrial division (fission) inhibitors. We compared two different inhibitors, mdivi-1 and 8-bromo-cyclic adenosine-mono-phosphate (8-bromo-cAMP), as they were demonstrated to show large effects on mitochondrial dynamics. After conducting preliminary confocal imaging, we found that 8-bromo-cAMP exhibited the largest effect on mitochondria distribution. We collected image data and performed mitochondrial morphology analysis of 30 untreated J774A.1 cells and 30 cells after treating them with 8-bromo-cAMP. A representative comparison of 3D reconstructed volumetric images is shown in FIG. 9A. Because of isotropic spatial resolution offered by the method, we were able to calculate absolute volumes of mitochondrial clusters.

Figures 9D, 9E:
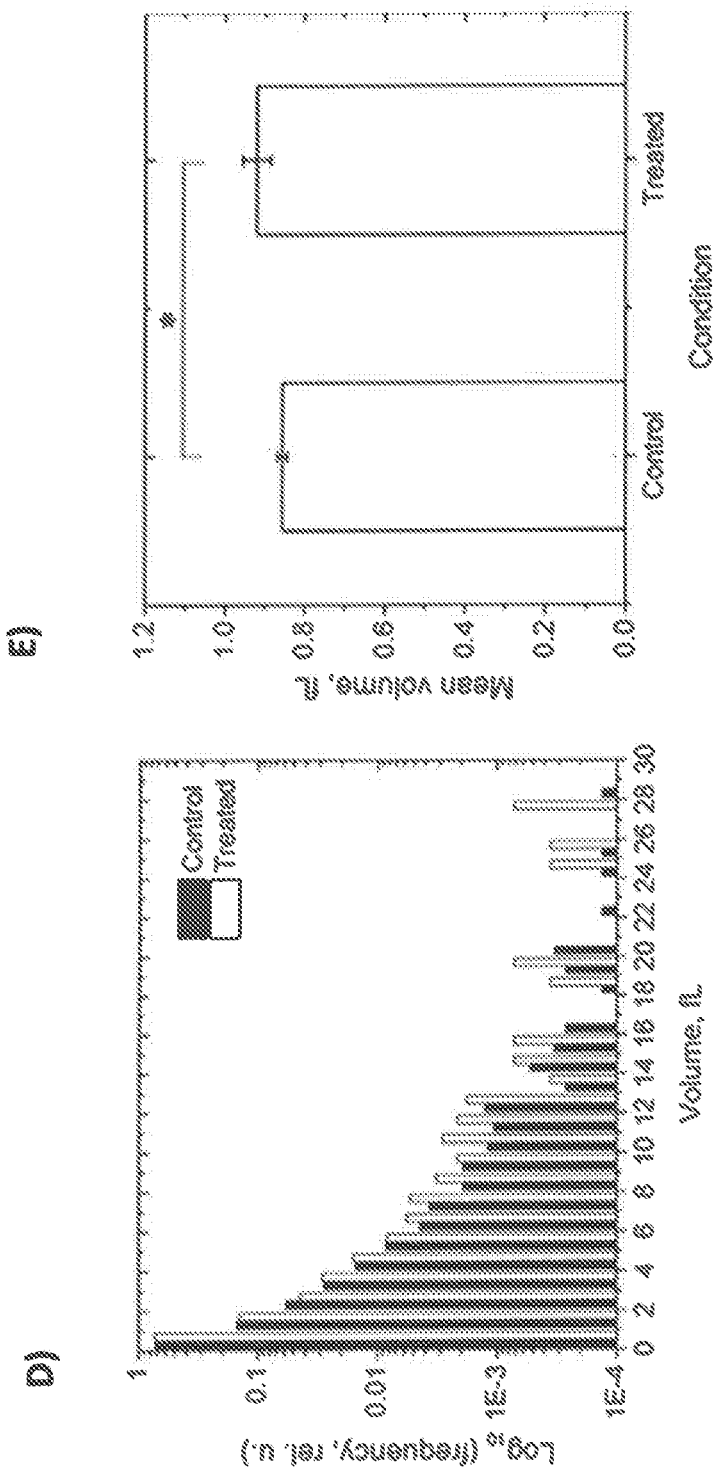
FIG. 9D shows combined mitochondrial structures volume distribution of 30 control and 30 treated cells. A trend toward increasing volume of the structures can be seen.
FIG. 9E shows the average values of the volume distribution shows less pronounced, but statistically significant ($p=0.008$, Kolmogorov-Smirnov test) increase in the mitochondrial volume in treated vs. control cells.

We developed a custom computational pipeline for processing reconstructed 3D images. The pipeline includes the background subtraction, contrast enhancement through intensity normalization steps, followed by adaptive local thresholding using the Niblack method[32], and a 3D object counting steps based on the nearest neighborhood connectivity. As expected, we observed marked alterations in the mitochondrial distribution, namely in a fraction of cells formation of large clusters as compared with seemingly smaller, more diffusely distributed mitochondrial structures in untreated cells (FIG. 9B, C). Interestingly, not all cells exhibited such dramatic changes in mitochondrial distribution. After a close examination of all recorded datasets it became clear that a portion of the treated cells exhibited less marked changes in the mitochondrial volume. A detailed analysis of the entire sample revealed a less pronounced, but statistically significant increase in the average volume of mitochondrial structures after treatment (FIG. 9D, E).

While our developed image processing and feature extraction pipeline gave satisfactory results, we also know that it can be improved to better account for the interconnectivity between the mitochondria. Custom computational tools and optimized pipelines need to be developed to account for specific aspects of features such as joining, intensity variation, local noise patterns, etc. Improved feature extraction pipelines specifically tailored towards 3D volumetric imagery of cells in suspension would benefit full utilization of the quantitative aspect of the approach.

Mitochondrial and Nuclear Dynamics Studies

Figures 10A, 10B:
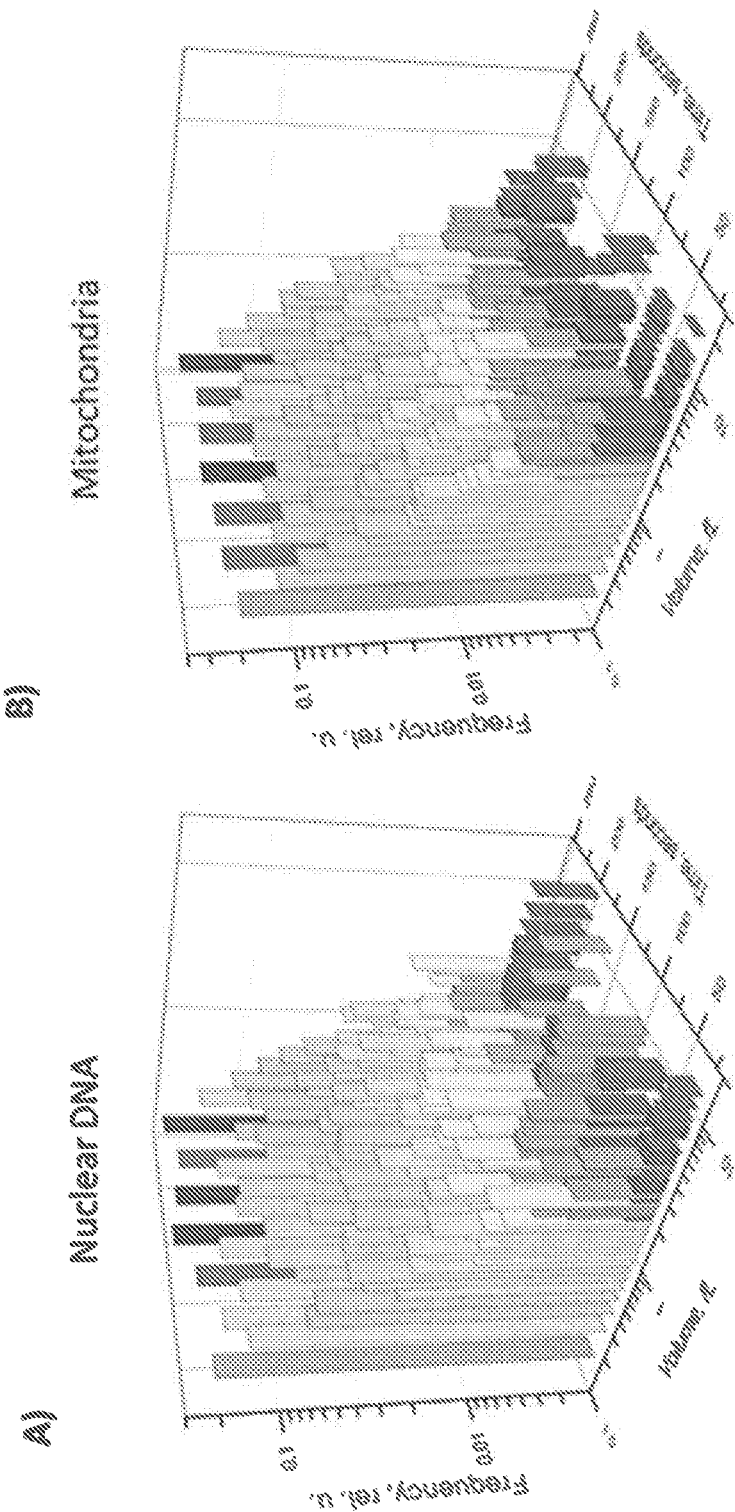
FIG. 10A shows alterations in the nuclear DNA spatial distribution. The graph shows changes in the volume distribution over time, revealing most dynamics in the structures with larger (2-12 fL) volumes, whereas the smaller features show little change.
FIG. 10B demonstrated mitochondrial structure dynamics, which showed qualitatively similar behavior as the nucleus. The majority of changes can be seen in the structures with larger (3-20 fL) volumes, while the smaller structures show relatively little alteration.

We next conducted a series of experiments in which we used the LCCT platform to explore intrinsic temporal characteristics of nuclear and mitochondrial morphology in mouse macrophages (J774A.1 cell line). For each cell we acquired projection images over a time period of ~3-5 minutes during continuous rotation a temporal resolution of 30 seconds. We acquired nuclear and mitochondrial morphology data for a total of 30 J774A.1 cells. The data analysis of the reconstructed 3D images was performed using a similar analysis pipeline as outlined in the mitochondrial fission inhibition study above. Briefly, the images were background subtracted and a local adaptive threshold was applied. After intensity normalization features were extracted using a 3D object counting routine based on nearest neighborhood connectivity. Data shows a representative time-lapse 3D reconstruction of a J774A.1 cell. We extracted and calculated features for both mitochondria and the nucleus. Due to isotropic spatial resolution provided by the LCCT method, we could determine a number of quantitative morphology characteristics, including feature volumes, positions of the centroids and center of mass with respect to the 3D volume, and mean densities. FIG. 10 shows a typical dataset of feature volume distribution over time for the cell. In general, we observed that features in the lower range of volumes (0.01-0.1 fL) show markedly less temporal variation in volume as compared to the larger structures (0.1-0.3 fL).

Discussion

We believe this is the first report of immune system cells imaged in suspension with isotropic 3D spatial resolution. Furthermore, absolute volumetric data of nuclear and mitochondrial distribution and dynamics have been obtained. We note that many other commercial fluorophores can be utilized to target other organelles or proteins in live cells. Our experimental findings indicate that a majority of mitochondria in suspension cells are highly interconnected forming a complex and dynamic filamentous network. The quantification of mitochondrial and nuclear remodeling over time enables direct multi-parameter comparisons between individual cells or cell types offering a unique way for rare cell identification with high accuracy. The quantitative data obtained with LCCT is amenable for multiparameter characterization of cellular phenotypes with improved sensitivity and specificity as compared to other, semi-quantitative imaging modalities.

The isotropic 3D spatial resolution provided by LCCT enables absolute measurements at the diffraction limit. Spectrally resolved imaging permits simultaneous detection and correlation of structural and functional alterations in different organelles and/or regions of the cell. The number of spectral channels can be increased by spectrally splitting emission photons onto different quadrants of the detector or using additional detectors. Although here we present only a limited number of morphometric nuclear and mitochondrial features, the set of quantitative features can be expanded markedly by adding a variety of established textural measures to the computational quantification pipeline. This would not only increase the amount of detail obtainable on a single-cell basis, but may also substantially improve statistical power of differentiating cell subtypes. While current spatial resolution of the method is diffraction-limited, it is conceivable that some of the advanced superresolution imaging modalities may be combined to surpass the diffraction limit. Modalities based on single emitter localization (STORM, PALM) or stimulated emission depletion (STED) via engineered PSF may be too slow for imaging of densely stained entire cells and/or damaging to make such a combination biologically reasonable. On the other hand, modalities such as structured illumination microscopy (SIM) or image scanning microscopy (ISM), which both offer about two fold increase in spatial resolution, appear feasible candidates. Due to their wide field image acquisition mode, which is directly compatible with LCCT, both SIM and ISM could be used to acquire projection images with resulting isotropic resolution of 125-150 nm.

We note that the mitochondria of the suspended cells (FIGS. 8 and 9) appear different from what one would typically expect from confocal imaging of mitochondria in cells adhered to a planar substrate. Namely, in adherent cells with most of the mitochondria located in a flattened thin layer of the cytoplasm, one can usually observe individual mitochondria in the shape of elongated string-shaped or round structures. Contrary to separate mitochondria, mitochondria in our images appear distributed around the nucleus and form a complex, dense 3D network partially in form of clusters of varying size. It is possible that this appearance of the mitochondria is due to three not mutually exclusive causes: 1) Mitochondria movement during imaging; 2) Cell type specificity; and/or 3) Imaging immune systems cells in their natural conformation—suspension—, as opposed to adhered to a planar substrate. Our confocal images of the mitochondria in fixed K562 cells revealed a qualitatively similar appearance of the mitochondria as in live cells, suggesting that mitochondrial movement on the time scale of 30 seconds or less in the two studied cell types may be considered as a relatively minor factor in LCCT imaging. We therefore conclude that the observed mitochondrial morphology can be attributed to the cell type specificity and/or the fact that the cells are imaged suspended in 3D space rather than adhered on a planar substrate.

We demonstrated a temporal resolution of our method of ~30 seconds (time needed to acquire a full set of 2D projections of the cell in one or more embodiments) which is mainly limited by the speed of scanning the objective lens. It is conceivable that cellular events taking place on a second scale, e.g. mitochondrial fusion and fission, are detected as temporal averages resulting in blurring of the rapidly altering structures. Faster, resonant scanner systems can be employed to increase the scan speed 5-fold or more resulting in improved temporal resolution. Depending on the properties of the fluorescent label, photobleaching and resulting phototoxicity may become a limiting factor for time-lapse imaging experiments. Different illumination schemes, such as selective plane illumination or HiLo may be integrated into our system to alleviate the issue of photobleaching and increase imaging contrast.

In summary, the presented method is a powerful and versatile tool for investigating cellular dynamics in cell suspensions in a quantitative fashion by enabling measurements in 3D space with diffraction limited spatial resolution. The approach enables quantitative studies of cellular architecture dynamics and could be utilized for combined nuclear and mitochondrial organization studies in response to treatment.

We claim:

1. An optical computed tomography (CT) system, comprising:
    a frame having a first plane comprising a first axis and a second plane comprising a second axis, wherein the first plane is substantially orthogonal to the second plane and the first axis is substantially orthogonal to the second axis, wherein the frame further comprises a first platform positioned along the first plane that is able to move along the first axis, the second axis, and a third axis, wherein the third axis is disposed with the first plane and is substantially transverse to the first axis, and wherein the frame further comprises a second platform positioned along the second plane;

a device manifold supported by said frame and disposed parallel to said first plane, wherein the device manifold further comprises a microfluidic module comprising at least one imaging chamber having an inlet to receiving an object and an outlet for dispensing the object, wherein the imaging chamber comprises a plurality of microelectrodes configured to induce rotation of the object as a result of an induced dipole moment in the object;

a first optical train connected to said first platform and disposed along said second axis, the first optical train comprising a light source that delivers light to the object and a camera configured to receive an emission signal from the object;

a second optical train connected to said second platform and disposed along said second axis, the second optical train comprising a light source that delivers light to the object and a camera configured to receive transmitted light from the object; and a computer in electrical communication with the plurality of microelectrodes and the first optical train, the computer programmed to:
  rotate, using the plurality of microelectrodes, the object to complete a 360 degree rotation;
  acquire a two dimensional (2D) pseudo-projection image of the object during rotation to form a plurality of 2D pseudo-projection images of the object;
  construct a 3D image of the object based on said plurality of 2D pseudo-projection images of the object, and
wherein the 2D pseudo-projections are collected at an angular sampling rate from 0.72 degrees to 1.2 degrees over the 360 degree rotation of the object.

2. The system of claim 1, wherein
the object is selected from the group consisting of a live cell, live multicellular duster, fixed cell, fixed multicellular cluster, live tissue, fixed tissue, and any combinations thereof.

3. The system of claim 1, wherein the device manifold is connected to and disposed on the first platform.

4. The system of claim 1, wherein the microfluidic module further comprises a fluid pumping apparatus comprising an air pressure controller, a vacuum controller, a fluid reservoir, and a flow monitoring device, wherein the fluid pumping apparatus collects the object and delivers the object to a container.

5. The system of claim 1, wherein the first optical train comprises a scanning objective.

6. The system of claim 1, wherein the second optical train comprises an object trapping region configured to trap the object.

7. The system of claim 1, wherein the camera is an electron-multiplying charge-coupled device (EMCCD) or a scientific complementary metal-oxide-semiconductor (sCMOS) camera.

8. The system of claim 1, wherein is configured to deliver a laser light.

9. The system of claim 1, wherein the computer is further programmed to: rotate the cell at a rotation speed from 1 to 2.5 rotation per minute (rpm).

10. The system of claim 1, wherein the computer is further programmed to:
  subtract background from the 3D image;
  enhance contrast using intensity normalization;
  apply an adaptive local threshold to the 3D image; and
  extract a feature using a 3D object count based on nearest neighborhood connectivity.

11. The system of claim 10, wherein the feature is selected from one or more of a volume of the object, position of a centroid of the object, a center of mass of the object, or a mean density of the object.

12. The system of claim 10, wherein the adaptive local threshold is applied using a Niblack method.

13. An optical computed tomography (CT) system, comprising:
  a frame having a first plane comprising a first axis and a second plane comprising a second axis, wherein the first plane is substantially orthogonal to the second plane and the first axis is substantially orthogonal to the second axis, wherein the frame further comprises a first platform positioned along the first plane that is able to move along the first axis, the second axis, and a third axis, wherein the third axis is disposed with the first plane and is substantially transverse to the first axis, and wherein the frame further comprises a second platform positioned along the second plane;
  a device manifold supported by said frame and disposed parallel to said first plane, wherein the device manifold further comprises a microfluidic module comprising at least one imaging chamber having an inlet to receiving an object and an outlet for dispensing the object, wherein the imaging chamber comprises a plurality of microelectrodes configured to induce rotation of the object as a result of an induced dipole moment in the object;
  a first optical train directly connected to said first platform and disposed along said second axis, the first optical train comprising a light source that delivers light to the object and a camera configured to receive an emission signal from the object; and
  a second optical train directly connected to said second platform and disposed along said second axis, the second optical train comprising a light source that delivers light to the object and a camera configured to receive transmitted light from the object.

* * * * *